(12) United States Patent
Goto et al.

(10) Patent No.: US 9,480,772 B2
(45) Date of Patent: Nov. 1, 2016

(54) GEL SHEET CONTAINING LIPID PEPTIDE GELATOR AND POLYMERIC COMPOUND

(75) Inventors: Masahiro Goto, Fukuoka (JP); Takayuki Imoto, Funabashi (JP); Tsubasa Kashino, Funabashi (JP); Takehisa Iwama, Funabashi (JP); Nobuhide Miyachi, Tokyo (JP)

(73) Assignees: NISSAN CHEMICAL INDUSTRIES, LTD., Tokyo (JP); KYUSHU UNIVERSITY, Fukuoka-shi (JP)

( * ) Notice: Subject to any disclaimer, the term of this patent is extended or adjusted under 35 U.S.C. 154(b) by 411 days.

(21) Appl. No.: 13/885,099

(22) PCT Filed: Nov. 11, 2011

(86) PCT No.: PCT/JP2011/076109
§ 371 (c)(1),
(2), (4) Date: Jul. 15, 2013

(87) PCT Pub. No.: WO2012/063947
PCT Pub. Date: May 18, 2012

(65) Prior Publication Data
US 2013/0296761 A1 Nov. 7, 2013

(30) Foreign Application Priority Data
Nov. 12, 2010 (JP) .................................. 2010-253736

(51) Int. Cl.
| | | |
|---|---|---|
| A61L 26/00 | (2006.01) | |
| A61K 9/00 | (2006.01) | |
| A61K 9/06 | (2006.01) | |
| A61K 8/65 | (2006.01) | |
| A61K 8/73 | (2006.01) | |
| A61Q 19/00 | (2006.01) | |
| A61K 8/81 | (2006.01) | |
| A61K 8/02 | (2006.01) | |
| A61K 9/70 | (2006.01) | |
| A61K 8/49 | (2006.01) | |
| A61K 8/04 | (2006.01) | |

(52) U.S. Cl.
CPC .......... *A61L 26/0095* (2013.01); *A61K 8/0216* (2013.01); *A61K 8/042* (2013.01); *A61K 8/4946* (2013.01); *A61K 8/65* (2013.01); *A61K 8/73* (2013.01); *A61K 8/8129* (2013.01); *A61K 9/0014* (2013.01); *A61K 9/06* (2013.01); *A61K 9/7015* (2013.01); *A61L 26/008* (2013.01); *A61L 26/0052* (2013.01); *A61Q 19/00* (2013.01); *A61K 2800/10* (2013.01)

(58) Field of Classification Search
CPC .................................................. A61L 26/0095
See application file for complete search history.

(56) References Cited

U.S. PATENT DOCUMENTS

| 5,503,776 A | * | 4/1996 | Murase ................. A23L 3/3526 252/397 |
|---|---|---|---|
| 2003/0165560 A1 | * | 9/2003 | Otsuka et al. ................. 424/445 |
| 2009/0297587 A1 | | 12/2009 | Yang et al. |
| 2010/0279955 A1 | * | 11/2010 | Miyachi et al. ............. 514/21.9 |
| 2010/0291210 A1 | | 11/2010 | Miyachi et al. |

FOREIGN PATENT DOCUMENTS

| EP | 2 494 953 A1 | 9/2012 |
|---|---|---|
| JP | A-6-313064 | 11/1994 |
| JP | A-9-267453 | 10/1997 |
| JP | B2-3107488 | 11/2000 |
| JP | A-2009-102228 | 5/2009 |
| JP | A-2010-95586 | 4/2010 |
| WO | WO 02/22182 A1 | 3/2002 |
| WO | WO 2009/005151 A1 | 1/2009 |
| WO | WO 2009/005152 A1 | 1/2009 |
| WO | WO 2010/013555 A1 | 2/2010 |
| WO | WO 2011/052613 A1 | 5/2011 |

OTHER PUBLICATIONS

Takamura et al., "Drug Release from Freeze-Thaw Poly(vinyl alcohol) Gel," *Yakugaku Zasshi*, 1987, vol. 107, No. 3, pp. 233-237 (with Abstract).
Matsumoto et al., "The Supramolecular Hydrogel toward 'The Smart Biomaterials,'" *Dojin News*, 2006, No. 118, pp. 1-16 (with Abstract).
Estroff et al., "Water Gelation by Small Organic Molecules," *Chemical Reviews*, 2004, vol. 104, No. 3, pp. 1201-1217.
Suzuki et al., "Supramolecular Hydrogels Formed by $_L$-Lysine Derivatives," *Chemistry Letters*, 2004, vol. 33, No. 11, pp. 1496-1497.
Jung et al., "Self-Assembly of a Sugar-Based Gelator in Water: Its Remarkable Diversity in Gelation Ability and Aggregate Structure," *Langmuir*, 2001, vol. 17, pp. 7229-7232.
Itaru et al., "Solid-Phase Lipid Synthesis (SPLS)-2: Incidental Discovery of Organogelators Based on Artificial Glycolipids," *Tetrahedron Letters*, 2001, vol. 42, pp. 6141-6145.
Hamachi et al., "Solid Phase Lipid Synthesis (SPLS) for Construction of an Artificial Glycolipid Library," *Chem. Commun.*, 2000, pp. 1281-1282.

(Continued)

*Primary Examiner* — Amber D Steele
(74) *Attorney, Agent, or Firm* — Oliff PLC

(57) ABSTRACT

There is provided a gel sheet that has high biocompatibility and safety, can contain both a hydrophilic medicinal agent and a hydrophobic medicinal agent, and provides an excellent feel in use during the application onto human skin or others. A gel sheet including: a lipid peptide gelator including a low molecular weight lipid peptide having a molecular weight of 1,000 or less or a pharmaceutically usable salt of the lipid peptide; and a polymeric compound, wherein the polymeric compound is included in an amount of more than 1% (w/w) and less than 50% (w/w) with respect to the total mass of the gel sheet.

22 Claims, 6 Drawing Sheets

(56) References Cited

OTHER PUBLICATIONS

Suzuki et al., "Supramolecular Hydrogel Formed by Glucoheptonamide of $_L$-Lysine: Simple Preparation and Excellent Hydorgelation Ability," *Tetrahedron*, 2007, vol. 63, pp. 7302-7308.

Matsuzawa et al., "Assembly and Photoinduced Organization of Mono- and Oligopeptide Molecules Containing an Azobenzene Moiety," *Advanced Functional Materials*, 2007, vol. 17, pp. 1507-1514.

International Search Report issued in International Patent Application No. PCT/JP2011/076109 dated Dec. 6, 2011.

Jun. 18, 2015 Supplementary European Search Report issued in European Application No. 11839325.5.

* cited by examiner

LAMELLAR STRUCTURE (A)

(B)

GEL SHEET CONTAINING LIPID PEPTIDE GELATOR AND POLYMERIC COMPOUND

TECHNICAL FIELD

The present invention relates to a gel sheet and more specifically relates to a gel sheet including a low molecular weight lipid peptide gelator and a polymeric compound.

BACKGROUND ART

A sheet-shaped gel that is obtained by forming a gel, especially a hydrogel, into a sheet shape has been used in cosmetic and medical care fields, for example, as a pack and an adhesive patch for beauty, skin treatment, and other purposes, as a carrier of an active component such as a skin penetrating component and an anti-inflammatory analgesic, as a pressure-sensitive adhesive tape for living bodies for wound protection, pharmaceutical drug immobilization, and other purposes, and as a wound dressing. In these applications, a sheet-shaped gel is typically formed as a water-containing gel layer on a sheet-shaped support medium to be used, and the support medium commonly used is a nonwoven fabric made of polyester, polypropylene, or the like (Patent Document 1).

The hydrogel commonly includes a natural product, an organic-inorganic composite hydrogel, and a synthetic polymer as its base material. Examples of the gel base material derived form a natural, product include polysaccharides such as hyaluronic acid, xanthan gum, gellan gum, agarose, carrageenan, and gum arabic.

A gel including such a gel base material derived from a natural product such as these natural polysaccharides has a problem of low strength and poor flexibility. In order to solve such a problem, for example, a method of adding, as a gel reinforcing agent, a methacryl resin powder having a polymethyl(meth)acrylate functional group, an aqueous solution of an acrylic polymer having the functional group, polyethylene glycol, etc. (Patent Document 2), a method of increasing the strength by chemically cross-linking with, for example, an epoxy compound cross-linking agent (Patent Document 3), and other methods have been disclosed. However, a remaining monomer of the gel reinforcing agent or a remaining cross-linking agent is difficult to be completely removed after the gel formation, and thus using the gel for cosmetics, external preparations, and other purposes involves many problems.

It has been also reported that an organic-inorganic composite hydrogel (nanocomposite gel) obtained by using delaminated clay as a super-multifunctional cross-linking agent is subjected to pressurization treatment, decompression treatment, or drawing treatment under drying/heating conditions so that the hydrogel can be formed into a film shape, a fibrous shape, or the like while maintaining high-strength and high-elongation characteristics (Patent Document 4), but it is pointed out that the production process is complicated.

In contrast, a synthetic polymer gel a gel obtained by cross-linking polymer chains with each other with an organic cross-linking agent or under irradiation of γ-rays or electron beams. For example, a polyvinyl alcohol (PVA) hydrogel obtained by the cross-linking of PVA in an aqueous solution under the irradiation of radiation rays is expected as a biocompatible material such as a wound dressing. Previously reported examples of the production method include a method in which an aqueous PVA solution is dried and heated and the treated PVA is irradiated with radiation rays so as to afford a PVA hydrogel laminate having an increased strength (Patent Document 5), but such a method includes too complicated processes to be industrialized.

PVA is commonly used as a thickener and a coating and film forming agent and is difficult to prepare a gel having high strength. Thus, known methods for preparing a sheet from such PVA include a complicated production method of repeating a freezing and thawing process and a production method of cross-linking PVA with glutaraldehyde (Non-Patent Document 1). However, such a method involves complicated procedures or may cause a monomer (glutaraldehyde) to be mixed in the gel, which has a risk of stimulating skins or wounds when the gel is used as cosmetics or external preparations. On this account, there is a demand for a gel that is produced by a simple method and that includes highly safe materials.

A carboxy vinyl polymer or a carboxy vinyl polymer derivative is often used for gel formation from the standpoint of easy production and flexibility. The gelation of the carboxy vinyl polymer requires a neutralizing agent, so skin irritation and instability caused by the neutralizing agent is required to be improved.

To address these problems, the function of a hydrogelator including a low molecular weight compound has been drawing increasing attention, although the mechanism elucidation of self-organization of the low molecular weight compound in water and molecular design are difficult. Thus, such a hydrogelator has been actively studied. As a result, some low molecular hydrogelators have been found (Non-Patent Document 2 and Non-Patent Document 3). Most of them are amphiphilic compounds combining a long-chain alkyl group as a hydrophobic moiety with a hydrophilic moiety, and examples thereof include an amphiphilic compound having an amino acid as the hydrophilic moiety (Non-Patent Document 4), an amphiphilic compound having a peptide as the hydrophilic moiety (Patent Document 6 and Patent Document 7), an amphiphilic compound having a mono- or poly-saccharide as the hydrophilic moiety (Non-Patent Document 5, Non-Patent Document 6, and Non-Patent Document 7), and an amphiphilic compound having a polyol as the hydrophilic moiety (Non-Patent Document 8). In addition, a low molecular weight gelator utilizing that a peptide including valine readily forms a β-sheet structure is also disclosed (Non-Patent Document 9).

RELATED ART DOCUMENTS

Patent Documents

Patent Document 1: Japanese Patent Application Publication No. 2009-102228 (JP 2009-102228 A)

Patent Document 2: Japanese Patent Application Publication No. 6-313064 (JP 6-313064 A)

Patent Document 3: Japanese Patent No. 3107488

Patent Document 4: Japanese Patent Application Publication No. 2010-95586 (JP 2010-95586 A)

Patent Document 5: Japanese Patent Application Publication No. 9-267453 (JP 9-267453 A)

Patent Document 6: International Publication WO 2009/005151 pamphlet

Patent Document 7: International Publication WO 2009/005152 pamphlet

Non-Patent Documents

Non-Patent Document 1: Yakugaku Zasshi, 107, 233-237
Non-Patent Document 2: Shinji Matsumoto, Itaru Hamachi, Dojin News, No. 118, 1-16 (2006)
Non-Patent Document 3: Lara A. Estroffand, Andrew D. Hamilton, Chemical Review, 2004, 104, 1201-1217
Non-Patent Document 4: Suzuki, Masahiro; Yumoto, Mariko; Kimura, Mutsumi; Shirai Hirofusa; Hanabusa, Kenji, Chemistry Letters, 2004, 33 (11), 1496-1497
Non-Patent Document 5: Jong Hwa Jung, Geoerg John, Mitsutoshi Masuda, Kaname Yoshida, Seiji Shinkai, and Toshimi Shimizu, Langmuir 2001, 17, 7229-7232
Non-Patent Document 6: I. Hamachi, S. Kiyonaka, S. Shinkai, Tetrahedron Lett., 2001, 42, 6141
Non-Patent Document 7: I. Hamachi, S. Kiyonaka, S. Shinaki, Chem. Commun., 2000, 1281
Non-Patent Document 8: Masahiro Suzuki, Sanae Owa, Hirofusa Shirai, and Kenji Hanabusa, Tetrahedron, 2007, 63, 7302-7308
Non-Patent Document 9: Yoko Matsuzawa, Katsuyuki Ueki, Masaru Yoshida, Nobuyuki Tamaoki, Tohru Nakamura, Hideki Sakai, and Masahiko Abe, Adv. Funct. Mater., 2007, 17, 1507-1514

SUMMARY OF THE INVENTION

Problem to be Solved by the Invention

As discussed above, a sheet-shaped hydrogel is expected to be applied in cosmetic and medical care fields. However, the sheet-shaped hydrogel is required to include no cross-linking agent harmful to human health, include highly biocompatible and safe materials. In addition, in order to actually use the sheet-shaped hydrogel, the hydrogel is required to have excellent strength and flexibility and to provide an excellent feel in use such as good adhesive properties to skin. However, no sheet-shaped hydrogels disclosed in related arts satisfy all the requirements.

Although some gelators including a low molecular weight compound as the highly biocompatible and safe material and some hydrogels including the gel are disclosed, there is no report of a sheet-shaped functional hydrogel that uses a gelator including a low molecular weight compound and is formed by utilizing a self-organizing structure.

In view of the above, it is an object of the present invention to provide a gel sheet that has high biocompatibility and safety, can contain both a hydrophilic medicinal agent and a hydrophobic medicinal agent, and provides an excellent feel in use during the application onto human skin or others.

Means for Solving the Problem

As a result of intensive studies in order to solve the problems, the inventors of the present invention have found that a gel sheet including a lipid peptide gelator containing a low molecular weight lipid peptide or a pharmaceutically usable salt of the lipid peptide and a polymeric compound has excellent biocompatibility and safety, has sufficient strength and flexibility, and provides an excellent feel in use during the application onto skin, and have completed the present invention.

The inventors of the present invention have further repeated the study on the application of the gel sheet of the present invention to a wound dressing, while considering that the use of an alcohol (ethanol), which highly irritates skin, as a solvent or others should be avoided, have consequently found that adding a lactic acid salt allows a gel sheet having sufficient strength and flexibility to be afforded without using the alcohol as a solvent or others, and have completed the present invention.

That is, the present invention relates to, as a first aspect, a gel sheet that includes a lipid peptide gelator including a low molecular weight lipid peptide having a molecular weight of 1,000 or less or a pharmaceutically usable salt of the lipid peptide and a polymeric compound, wherein the polymeric compound is included in an amount of more than 1% (w/w) and less than 50% (w/w) with respect to the total mass of the gel sheet.

As a second aspect, the present invention relates to the gel sheet according to the first aspect, in which the polymeric compound is included in an amount of 2% (w/w) to 20% (w/w) with respect to the total mass of the gel sheet.

As a third aspect, the present invention relates to the gel sheet according to the first aspect, in which the polymeric compound is selected from a linear polymeric compound having a hydroxy group and polysaccharides.

As a fourth aspect, the present invention relates to the gel sheet according to the third aspect, in which the polymeric compound is polyvinyl alcohol, gum arabic, or gelatin.

As a fifth aspect, the present invention relates to the gel sheet according to the first aspect, in which the low molecular weight lipid peptide is a lipid peptide of Formula (1):

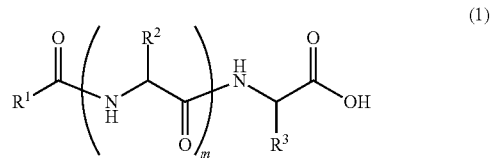

(where $R^1$ is a $C_{9-23}$ aliphatic group; each of $R^2$ and $R^3$ is independently a hydrogen atom, a methyl group, an ethyl group, a $C_{3-7}$ alkyl group optionally having a $C_{1-3}$ branched chain, a phenylmethyl group, a phenylethyl group, or a —$(CH_2)$n-X group, at least one of $R^2$ and $R^3$ being a —$(CH_2)$n-X group; n is a number of 1 to 4; X is an amino group, a guanidino group, a carbamoyl group, a 5-membered cyclic group or 6-membered cyclic group optionally having one to three nitrogen atoms, or a condensed heterocyclic group composed of a 5-membered ring and a 6-membered ring; and m is an integer of 1 to 3) or a pharmaceutically usable salt of the lipid peptide.

As a sixth aspect, the present invention relates to the gel sheet according to the fifth aspect, in which $R^2$ is a hydrogen atom, a methyl group, an i-propyl group, an i-butyl group, or a sec-butyl group.

As a seventh aspect, the present invention relates to the gel sheet according to the fifth aspect, in which $R^3$ is a 4-aminobutyl group, 4-imidazolemethyl group, a carbamoylmethyl group, a 2-carbamoylethyl group, or a 3-indolemethyl group.

As an eighth aspect, the present invention relates to the gel sheet according to the fifth aspect, in which $R^1$ is a $C_{13-17}$ aliphatic group, $R^2$ is a hydrogen atom, a methyl group, or an i-propyl group, and $R^3$ is a 4-aminobutyl group, a 4-imidazolemethyl group, or a 3-methylindole group.

As a ninth aspect, the present invention relates to the gel sheet according to the fifth aspect, in which $R^2$ is a hydrogen atom and $R^3$ is a 4-imidazolemethyl group.

As a tenth aspect, the present invention relates to the gel sheet according to any one of the first aspect to the ninth aspect, the gel sheet further including water, an alcohol, a polyhydric alcohol, a hydrophilic organic solvent, a hydrophobic organic solvent, or a mixed solution of two or more of these.

As an eleventh aspect, the present invention relates to the gel sheet according to the tenth aspect, in which the gel sheet includes water or a mixed solution of water and at least one selected from the group consisting of an alcohol, a polyhydric alcohol, an oil and fat, a silicone oil, and an ester solvent.

As a twelfth aspect, the present invention relates to the gel sheet according to the eleventh aspect, in which the gel sheet includes water or a mixed solution of water and at least one selected from the group consisting of ethanol, 2-propanol, oleyl alcohol, phenoxy alcohol, glycerin, propylene glycol, polyethylene glycol, 1,3-butanediol, aqua jojoba oil, castor oil, olive oil, a silicone oil, and propylene glycol alginate.

As a thirteenth aspect, the present invention relates to the gel sheet according to the tenth aspect, in which the gel sheet includes a polyhydric alcohol or a mixed solution of a polyhydric alcohol and at least one selected from the group consisting of an alcohol, an oil and fat, a silicone oil, and an ester solvent.

As a fourteenth aspect, the present invention relates to the gel sheet according to the thirteenth aspect, in which the gel sheet includes at least one polyhydric alcohol selected from the group consisting of glycerin, propylene glycol, polyethylene glycol, and 1,3-butanediol or a mixed solution of at least one of the polyhydric alcohols and at least one selected from the group consisting of ethanol, 2-propanol, oleyl alcohol, phenoxy alcohol, aqua jojoba oil, castor oil, olive oil, a silicone oil, and propylene glycol alginate.

As a fifteenth aspect, the present invention relates to the gel sheet according to the tenth aspect, in which the gel sheet includes a solution containing water and one lactic acid salt selected from the group consisting of potassium lactate, sodium lactate, and calcium lactate.

As a sixteenth aspect, the present invention relates to the gel sheet according to the fifteenth aspect, the gel sheet further including at least one polyhydric alcohol selected from the group consisting of glycerin, propylene glycol, polyethylene glycol, and 1,3-butylene glycol.

As a seventeenth aspect, the present invention relates to a laminate including the gel sheet as described in any one of the first aspect to the sixteenth aspect and a support medium laminated on the sheet, the support medium including a nonwoven fabric, a film, or a foam.

As an eighteenth aspect, the present invention relates to the laminate according to the seventeenth aspect, the laminate further including a release film laminated on a surface on the opposite side of the gel sheet from the support medium.

As a nineteenth aspect, the present invention relates to the laminate according to the seventeenth aspect, in which the support medium is selected from polyurethane, PVA, polypropylene, cellulose, and a laminated support medium of these.

As a twentieth aspect, the present invention relates to the gel sheet according to any one of the first aspect to the sixteenth aspect, the gel sheet being a wound dressing sheet.

As a twenty-first aspect, the present invention relates to the gel sheet according to any one of the first aspect to the sixteenth aspect, the gel sheet being a skin protection sheet or a skin care sheet.

As a twenty-second aspect, the present invention relates to the laminate according to any one of the seventeenth aspect to the nineteenth aspect, the laminate being used for a wound dressing.

As a twenty-third aspect, the present invention relates to the laminate according to any one of the seventeenth aspect to the nineteenth aspect, the laminate being used for a skin protection sheet or a skin care sheet.

Effects of the Invention

A gel sheet of the present invention can be easily obtained from a lipid peptide gelator having a low molecular weight. The gel sheet requires no cross-linking agent that is required to form a related art gel and thus is a gel sheet having excellent biocompatibility and safety.

The gel sheet of the present invention can be easily formed into a sheet shape by mixing each component and heating, dissolving, and leaving the mixture, thereby eliminating the need for complicated procedures required in related arts.

The gel sheet of the present invention includes a solvent and especially a polymeric compound in addition to the lipid peptide gelator. Such a structure allows the gel sheet to have high strength and high elasticity in addition to characteristics of a related art gel. The lipid peptide gelator in the gel sheet of the present invention can reduce the amount of the polymeric compound, thereby increasing the amount of a solvent such as water. Therefore, when a gel sheet of the present invention is in contact with human skin, a sticky feel and a squeak feel to the skin due to an increased amount of the polymeric compound can be reduced and a feel in use such as a nice texture, a moist feel, and a cold feel can be improved.

Moreover, after the formation of a gel sheet of the present invention, immersing the gel sheet into an alcohol (for example, ethanol) allows the sheet to become robust and simultaneously to be disinfected and sterilized. The sheet can also be formed by immersion in a solution of a lactic acid salt in place of the immersion in an alcohol.

The gel sheet of the present invention has an advantageous effect that a hydrophilic medicinal agent or a hydrophobic medicinal agent or both of them can be contained.

The gel sheet of the present invention is therefore useful for applications to be in contact with human skin, for example, for medical materials and cosmetic materials, and is especially expected to be used as a material for wound dressings in which an alcohol should not be used.

BRIEF DESCRIPTION OF THE DRAWINGS

FIG. 12B: ×1000).

FIG. 16A: an N-palmitoyl-Gly-His frozen gel and thawed gel sheet; FIG. 16B: a PVA gel frozen and thawed gel; FIG. 16C: a hydrocolloid material; and FIG. 16D: a PVA cross-linked hydrogel).

MODES FOR CARRYING OUT THE INVENTION

Figure 1:
FIG. 1 is photographs each showing a drop of a gel that was obtained in Example 1 and that was placed on a glass petri dish and then was left overnight.

The present invention relates to a gel sheet including a lipid peptide gelator and a polymeric compound.

Each component will be described below.

[Lipid Peptide Gelator]

A gel sheet of the present invention is characterized by including at least one lipid peptide gelator containing a low molecular weight lipid peptide or a pharmaceutically usable salt of the lipid peptide.

The lipid peptide preferably has a molecular weight of 1,000 or less.

Examples of the low molecular weight lipid peptide include a lipid peptide of Formula (1) having a lipid moiety and a peptide moiety and a pharmaceutically usable salt of the lipid peptide.

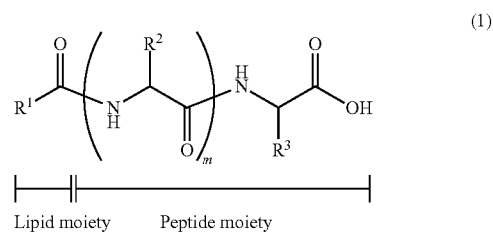

(1)

Lipid moiety    Peptide moiety

In Formula (1), $R^1$ is a $C_{9-23}$ aliphatic group and preferably a $C_{13-17}$ aliphatic group.

Examples of the lipid moiety including $R^1$ and the adjacent carbonyl group include a decoyl group, a dodecoyl group, an undecoyl group, a lauroyl group, a dodecylcarbonyl group, a myristoyl group, a tetradecylcarbonyl group, a palmitoyl group, a margaroyl group, an oleoyl group, an elaidoyl group, a linolcoyl group, a stearoyl group, a vaccenoyl group, an octadecylcarbonyl group, an arachidonoyl group, an icosanoyl group, a behenoyl group, an erucoyl group, a docosylcarbonyl group, a lignoceroyl group, and a nervonoyl group, and preferred examples include a myristoyl group, a tetradecylcarbonyl group, a palmitoyl group, a margaroyl group, an oleoyl group, an elaidoyl group, a linoleoyl group, a stearoyl group, and a vaccenoyl group.

In Formula (1), each of $R^2$ and $R^3$ is independently a hydrogen atom, a methyl group, an ethyl group, a $C_{3-7}$ alkyl group optionally having a $C_{1-3}$ branched chain, a phenylmethyl group, a phenylethyl group, or a $-(C_{1-2})n-X$ group, and at least one of $R^2$ and $R^3$ is a $-(CH_2)n-X$ group. n is a number of 1 to 4, and X is an amino group, a guanidino group, a carbamoyl group, a 5-membered cyclic group or 6-membered cyclic group optionally having one to three nitrogen atoms, or a condensed heterocyclic group composed of a 5-membered ring and a 6-membered ring.

Preferred $R^2$ is a hydrogen atom, a methyl group, an ethyl group, or a $C_{3-7}$ alkyl group optionally having a $C_{1-3}$ branched chain. Accordingly, $R^2$ is preferably a hydrogen atom, a methyl group, an ethyl group, an n-propyl group, an i-propyl group, an n-butyl group, an i-butyl group, a sec-butyl group, a tert-butyl group, or other groups, more preferably a hydrogen atom, a methyl group, an i-propyl group, an i-butyl group, or a sec-butyl group, and even more preferably a hydrogen atom.

Preferred $R^3$ is a hydrogen atom, a methyl group, or a $-(CH_2)n-X$ group. n is a number of 1 to 4, and X is an amino group, a guanidino group, a $-CONH_2$ group, or a 5-membered cyclic group or a 6-membered cyclic group optionally having one to three nitrogen atoms, or a condensed cyclic group including a 5-membered ring and a 6-membered ring.

Preferred $R^3$ is a hydrogen atom, a methyl group, or a $-(CH_2)n-X$ group. n is a number of 1 to 4, and X is an amino group, a guanidino group, a $-CONH_2$ group, or a 5-membered cyclic group or a 6-membered cyclic group optionally having one to three nitrogen atoms, or a condensed cyclic group including a 5-membered ring and a 6-membered ring.

In the $-(CH_2)n-X$ group of $R^3$, X is preferably an amino group, a guanidino group, a carbamoyl group, an imidazole group, a pyrazole group, or an indole group.

Accordingly, the —(CH$_2$)n-X group of R$^3$ is preferably an aminomethyl group, a 2-aminoethyl group, a 3-aminopropyl group, a 4-aminobutyl group, a carbamoylmethyl group, a 2-carbamoylethyl group, a 3-carbamoylpropyl group, a 2-guanidinoethyl group, a 3-guanidinopropyl group, a pyrrolemethyl group, a 4-imidazolemethyl group, a pyrazolemethyl group, or a 3-indolemethyl group, more preferably a 4-aminobutyl group, a carbamoylmethyl group, a 2-carbamoylethyl group, a 3-carbamoylpropyl group, a 4-imidazolemethyl group, or a 3-indolemethyl group, and even more preferably a 4-imidazolemethyl group.

In Formula (1), the number of repeats of the peptide structure in is an integer of 1 to 3.

In the compound of Formula (1), especially preferred lipid peptides as the lipid peptide gelator are the following compounds each formed of a lipid moiety and a peptide moiety. Here, the following abbreviation is used for each amino acid: asparagine (Asn); alanine (Ala); glutamine (Gln); glycine (Gly); valine (Val); histidine (His); lysine (Lys); and leucine (Leu). Examples of the compound include myristoyl-Gly-His, myristoyl-Gly-Lys, myristoyl-Gly-Asn, myristoyl-Gly-Gln, myristoyl-Gly-Gly-His, myristoyl-Gly-Gly-Lys, myristoyl-Gly-Gly-Asn, myristoyl-Gly-Gly-Gln, myristoyl-Gly-Gly-Gly-His, myristoyl-Gly-Gly-Gly-Lys, myristoyl-Gly-Gly-Gly-Asn, myristoyl-Gly-Gly-Gly-Gln, myristoyl-Ala-His, myristoyl-Ala-Lys, myristoyl-Ala-Asn, myristoyl-Ala-Gln, myristoyl-Ala-Ala-His, myristoyl-Ala-Ala-Lys, myristoyl-Ala-Ala-Asn, myristoyl-Ala-Ala-Gln, myristoyl-Ala-Ala-Ala-His, myristoyl-Ala-Ala-Ala-Lys, myristoyl-Ala-Ala-Ala-Asn, myristoyl-Ala-Ala-Ala-Gln, myristoyl-Val-His, myristoyl-Val-Lys, myristoyl-Val-Asn, myristoyl-Val-Gln, myristoyl-Val-Val-His, myristoyl-Val-Val-Lys, myristoyl-Val-Val-Asn, myristoyl-Val-Val-Gln, myristoyl-Val-Val-Val-His, myristoyl-Val-Val-Val-Lys, myristoyl-Val-Val-Val-Asn, myristoyl-Val-Val-Val-Gln, myristoyl-Leu-His, myristoyl-Leu-Lys, myristoyl-Leu-Asn, myristoyl-Leu-Gln, myristoyl-Leu-Leu-His, myristoyl-Leu-Leu-Lys, myristoyl-Leu-Len-Asn, myristoyl-Leu-Leu-Gln, myristoyl-Leu-Leu-Leu-His, myristoyl-Leu-Leu-Leu-Lys, myristoyl-Leu-Leu-Leu-Asn, myristoyl-Leu-Leu-Leu-Gln, palmitoyl-Gly-His, palmitoyl-Gly-Lys, palmitoyl-Gly-Asn, palmitoyl-Gly-Gln, palmitoyl-Gly-Gly-Lys, palmitoyl-Gly-Gly-His, palmitoyl-Gly-Gly-Gly-Asn, palmitoyl-Gly-Gly-Gly-Gln, palmitoyl-Ala-His, palmitoyl-Ala-Lys, palmitoyl-Ala-Asn, palmitoyl-Ala-Gln, palmitoyl-Ala-Ala-His, palmitoyl-Ala-Ala-Lys, palmitoyl-Ala-Ala-Asn, palmitoyl-Ala-Ala-Gln, palmitoyl-Ala-Ala-Ala-ills palmitoyl-Ala-Ala-Ala-Lys, palmitoyl-Ala-Ala-Ala-Asn, palmitoyl-Ala-Ala-Ala-Gln, palmitoyl-Val-His, palmitoyl-Val-Lys, palmitoyl-Val-Asn, palmitoyl-Val-Gln, palmitoyl-Val-Val-Lys, palmitoyl-Val-Val-Asn, palmitoyl-Val-Val-Gln, palmitoyl-Val-Val-Val-His, palmitoyl-Val-Val-Val-Lys, palmitoyl-Val-Val-Val-Asn, palmitoyl-Val-Val-Val-Gln, palmitoyl-Leu-His, palmitoyl-Leu-Lys, palmitoyl-Leu-Asn, palmitoyl-Leu-Gln, palmitoyl-Leu-Leu-His, palmitoyl-Leu-Leu-Lys, palmitoyl-Leu-Leu-Asn, palmitoyl-Leu-Leu-Gln, palmitoyl-Leu-Leu-Leu-His, palmitoyl-Leu-Leu-Leu-Lys, palmitoyl-Leu-Leu-Leu-Asn, palmitoyl-Leu-Leu-Leu-Gln, stearoyl-Gly-His, stearoyl-Gly-Lys, stearoyl-Gly-Asn, stearoyl-Gly-Gln, stearoyl-Gly-Gly-His, stearoyl-Gly-Gly-Lys, stearoyl-Gly-Gly-Asn, stearoyl-Gly-Gly-Gln, stearoyl-Gly-Gly-Gly-His, stearoyl-Gly-Gly-Gly-Lys, stearoyl-Gly-Gly-Gly-Asn, stearoyl-Gly-Gly-Gly-Gln, stearoyl-Ala-His, stearoyl-Ala-Lys, stearoyl-Ala-Asn, stearoyl-Ala-Gln, stearoyl-Ala-Ala-His, stearoyl-Ala-Ala-Lys, stearoyl-Ala-Ala-Asn, stearoyl-Ala-Ala-Gln, stearoyl-Ala-Ala-Ala-His, stearoyl-Ala-Ala-Ala-Lys, stearoyl-Ala-Ala-Ala-Asn, stearoyl-Ala-Ala-Ala-Gln, stearoyl-Val-His, stearoyl-Val-Lys, stearoyl-Val-Asn, stearoyl-Val-Gln, stearoyl-Val-Val-His, stearoyl-Val-Val-Lys, stearoyl-Val-Val-Asn, stearoyl-Val-Val-Gln, stearoyl-Val-Val-Val-His, stearoyl-Val-Val-Val-Lys, stearoyl-Val-Val-Val-Asn, stearoyl-Val-Val-Val-Gln, stearoyl-Leu-His, stearoyl-Leu-Lys, stearoyl-Leu-Asn, stearoyl-Leu-Gln, stearoyl-Leu-Leu-His, stearoyl-Leu-Leu-Lys, stearoyl-Leu-Leu-Asn, stearoyl-Leu-Leu-Gln, stearoyl-Leu-Leu-Leu-His, stearoyl-Leu-Leu-Leu-Lys, stearoyl-Leu-Leu-Leu-Asn, and stearoyl-Leu-Leu-Leu-Gln.

Most preferred examples of the compound include myristoyl-Gly-His, myristoyl-Gly-Gly-His, myristoyl-Gly-Gly-Gly-His, palmitoyl-Gly-His, palmitoyl-Gly-Gly-His, palmitoyl-Gly-Gly-Gly-His, stearoyl-Gly-His, stearoyl-Gly-Gly-His, and stearoyl-Gly-Gly-Gly-His.

Usable low molecular weight lipid peptides, besides the lipid peptide of Formula (1) or a pharmaceutically usable salt of the lipid peptide, include the following lipid peptides formed of a lipid moiety and an amino acid moiety or a peptide moiety. The abbreviation of each amino acid is as described above. Examples of the lipid peptide include myristoyl-His, myristoyl-Lys, myristoyl-Asn, myristoyl-Gln, myristoyl-Gly-Gly-Gly-Gly-His, myristoyl-Gly-Gly-Gly-Gly-Lys, myristoyl-Gly-Gly-Gly-Gly-Asn, myristoyl-Gly-Gly-Gly-Gln, myristoyl-Ala-Ala-Ala-Ala-His, myristoyl-Ala-Ala-Ala-Ala-Lys, myristoyl-Ala-Ala-Ala-Ala-Asn, myristoyl-Ala-Ala-Ala-Ala-Gln, myristoyl-Val-Val-Val-Val-His, myristoyl-Val-Val-Val-Val-Lys, myristoyl-Val-Val-Val-Val-Asn, myristoyl-Val-Val-Val-Val-Gln, myristoyl-Leu-Leu-Leu-Leu-His, myristoyl-Leu-Leu-Leu-Leu-Lys, myristoyl-Leu-Leu-Leu-Leu-Asn, myristoyl-Leu-Leu-Len-Leu-Gln; palmitoyl-His, palmitoyl-Lys, palmitoyl-Asn, palmitoyl-Gln, palmitoyl-Gly-Gly-Gly-Gly-His, palmitoyl-Gly-Gly-Gly-Gly-Lys, palmitoyl-Gly-Gly-Gly-Gly-Asn, palmitoyl-Gly-Gly-Gly-Gly-Gln, palmitoyl-Ala-Ala-Ala-Ala-His, palmitoyl-Ala-Ala-Ala-Ala-Lys, palmitoyl-Ala-Ala-Ala-Ala-Asn, palmitoyl-Ala-Ala-Ala-Ala-Gln, palmitoyl-Val-Val-Val-Val-His, palmitoyl-Val-Val-Val-Val-Lys, palmitoyl-Val-Val-Val-Val-Asn, palmitoyl-Val-Val-Val-Val-Gln, palmitoyl-Leu-Leu-Leu-Leu-His, palmitoyl-Leu-Leu-Leu-Leu-lys, palmitoyl-Leu-Leu-Leu-Leu-Asn, palmitoyl-Leu-Leu-Leu-Leu-Gln; stearoyl-His, stearoyl-Lys, stearoyl-Asn, stearoyl-Gln, stearoyl-Gly-Gly-Gly-Gly-His, stearoyl-Gly-Gly-Gly-Gly-Lys, stearoyl-Gly-Gly-Gly-Gly-Asn, stearoyl-Gly-Gly-Gly-Gly-Gln, stearoyl-Ala-Ala-Ala-Ala-His, stearoyl-Ala-Ala-Ala-Ala-Lys, stearoyl-Ala-Ala-Ala-Ala-Asn, stearoyl-Ala-Ala-Ala-Ala-Gln, stearoyl-Val-Val-Val-Val-His, stearoyl-Val-Val-Val-Val-Lys, stearoyl-Val-Val-Val-Val-Asn, stearoyl-Val-Val-Val-Val-Gln, stearoyl-Leu-Leu-Leu-Leu-His, stearoyl-Leu-Leu-Leu-Leu-Lys, stearoyl-Leu-Leu-Leu-Leu-Asn, and stearoyl-Leu-Leu-Leu-Gln.

Among them, preferred examples include myristoyl-His, myristoyl-Gly-Gly-Gly-Gly-His, palmitoyl-His, palmitoyl-Gly-Gly-Gly-Gly-His, stearoyl-His, and stearoyl-Gly-Gly-Gly-Gly-His.

[Polymeric Compound]

Examples of the polymeric compound included in the gel sheet of the present invention include guar gum, locust bean gum, quince seed, carrageenan, galactan, gum arable, tara gum, tamarind, furcellaran, karaya gum, *Abelmoschus manihot*, cam gum, gum tragacanth, pectin, pectic acid and salts thereof such as a sodium salt, alginic acid and salts thereof such as a sodium salt, and mannan; starches such as rice starch, corn starch, potato starch, and wheat starch; xanthan gum, dextran, succinoglucan, curdlan, hyaluronic acid and salts thereof, xanthan gum, pullulan, gellan gum, chitin, chitosan, agar, brown algae extract, chondroitin sulfate, casein, collagen, gelatin, and albumin; cellulose and derivatives thereof such as methyl cellulose, ethyl cellulose, hydroxyethyl cellulose, hydroxymethylpropyl cellulose, hydroxypropyl cellulose, carboxymethyl cellulose and salt thereof such as a sodium salt, methylhydroxypropyl cellulose, sodium cellulose sulfate, dialkyldimethylammonium cellulose sulfate, crystalline cellulose, and cellulose powder; starch derivatives such as soluble starch, starch polymers including carboxymethyl starch, methylhydroxypropyl starch, and methyl starch, starch hydroxypropyltrimonium chloride, and aluminum corn starch octenylsuccinate; alginic acid derivatives such as sodium alginate and propylene glycol alginate; polyvinylpyrrolidone (PVP), polyvinyl alcohol (PVA), a vinylpyrrolidone-vinyl alcohol copolymer, and polyvinyl methyl ether; polyethylene glycol, polypropylene glycol, and a polyoxyethylene-polyoxypropylene copolymer; amphoteric methacrylic ester copolymers such as a (methacryloyloxyethylcarboxybetaine/alkyl methacrylate) copolymer and an (acrylate/stearyl acrylate/ethylamine oxide methacrylate) copolymer; a (dimethicone/vinyl dimethicone) crosspolymer, an (alkyl acrylate/diacetone acrylamide) copolymer, and an (alkyl acrylate/diacetone acrylamide) copolymer AMP; a partially saponified polyvinyl acetate, maleic acid copolymer; a vinylpyrrolidone-dialkylaminoalkyl methacrylate copolymer; an acrylic resin alkanolamine; polyester and water-dispersible polyester; polyacrylamide; a copolymer of a polyacrylic ester such as polyethyl acrylate, a carboxy vinyl polymer, polyacrylic acid and salts thereof such as a sodium salt, an acrylic acid-methacrylic acid ester copolymer; an acrylic acid-alkyl methacrylate copolymer; cationized cellulose such as polyquaternium-10, a diallyldimethylammonium chloride-acrylamide copolymer such as polyquaternium-7, an acrylic acid-diallyldimethylammonium chloride copolymer such as polyquaternium-22, an acrylic acid-diallyldimethylanimonium chloride-acrylamide copolymer such as polyquaternium-39, an acrylic acid-cationized methacrylic ester copolymer, an acrylic acid-cationized methacrylic amide copolymer, an acrylic acid-methyl acrylate-methacrylamidopropyltrimethylammonium chloride copolymer such as polyquaternium-47, and a methacryloyl chloride choline ester polymer; cationized polysaccharides such as a cationized oligosaccharide, a cationized dextran, and guar hydroxypropyltrimonium chloride; polyethyleneimine; a cationic polymer; a copolymer of 2-methacryloyloxyethyl phosphorylcholine and n-butyl methacrylate such as polyquaternium-51; polymer emulsions such as an acrylic resin emulsion, a polyethyl acrylate emulsion, a polyacrylalkyl ester emulsion, a polyvinyl acetate resin emulsion, a natural rubber latex, and a synthetic latex; nitrocellulose; polyurethanes and various copolymers of the polyurethanes; various silicones; various silicone copolymers such as an acrylic-silicone graft copolymer; various fluorine polymers; 12-hydroxystearic acid and salts thereof; dextrin fatty acid esters such as dextrin palmitate and dextrin myristate; silicic anhydride, fumed silica (silicic anhydride ultrafine particles), magnesium aluminum silicate, magnesium sodium silicate, a metallic soap, a metal dialkyl phosphate, bentonite, hectorite, organo-modified clay mineral, a sucrose fatty acid ester, and a fructooligosaccharide fatty acid ester; keratin, myosin, and actin; proteoglycans and substances having a sugar chain function, such as decorin and lumican; and peptides having a functional sequence such as RGD.

Among them, substances selected from linear polymeric compounds having a hydroxy group or polysaccharides are preferred and polyvinyl alcohol, gum arabic, or gelatin is most preferred.

[Gel Sheet]

The gel sheet of the present invention includes the polymeric compound in an amount of more than 1% (w/w) and less than 50% (w/w) with respect to the total mass of the gel sheet.

The polymeric compound is preferably included in an amount of 2% (w/w) to 20% (w/w) and more preferably in an amount of 5% (w/w) to 10% (w/w) with respect to the total mass of the gel sheet.

The gel sheet of the present invention includes the lipid peptide gelator at any concentration as long as the gel sheet can be formed. The concentration is preferably 0.0001 to 50% (w/w), more preferably 0.0001 to 20% (w/w), and even more preferably 0.1 to 5% (w/w), with respect to the total mass of the gel sheet. A lipid peptide gelator included in an amount of less than 0.0001% (w/w) may not provide the effect as a gelator, and a lipid peptide gelator included in an amount of more than 50% (w/w) may not provide the stability for storage for a long period of time. A lipid peptide gelator included in an amount of 0.0001 to 50% (w' w) can impart sensory characteristics such as a moist (damp) feel and a cold (cool) feel to a gel sheet obtained.

[Solvent]

The gel sheet of the present invention includes, in addition to the lipid peptide gelator and the polymeric compound, a solvent, that is water, an alcohol, a polyhydric alcohol, a hydrophilic organic solvent, a hydrophobic organic solvent, or a mixed solution of two or more of these.

Preferred examples of the water include clean water, purified water, hard water, soft water, natural water, deep-sea water, electrolytic alkali ion water, electrolytic acidic ion water, ion water, and cluster water.

The alcohol is a monohydric alcohol, for example, a $C_{1-6}$ alcohol that can be dissolved in water at any ratio. Specific examples thereof include, but are not limited to, methanol, ethanol, 2-propanol, i-butanol, and a higher alcohol specifically including oleyl alcohol and phenoxy alcohol.

The polyhydric alcohol is an alcohol having two or more hydroxy groups and examples thereof include propylene glycol, 1,3-butanediol, 2-ethyl-1,3-hexanediol, glycerin, isopentyldiol, ethylhexanediol, erythrulose, ozonized glycerin, caprylyl glycol, ($C_{15-18}$) glycol, ($C_{20-30}$) glycol, diethylene glycol, diglycerin, dithiaoctanediol, dipropylene glycol (DPG), thioglycerin, 1,10-decanediol, decylene glycol, triethylene glycol, trimethylhydroxymethylcyclohexanol, phytantriol, phenoxypropanediol, 1,2-butanediol, 2,3-butanediol, butylethylpropanediol, 1,2-hexanediol, hexylene glycol, pentylene glycol, methylpropanediol, menthane diol, lauryl glycol, polyethylene glycol, and polypropylene glycol.

The hydrophilic organic solvent means an organic solvent that is dissolved in water at any ratio except alcohols and polyhydric alcohols. Examples of the hydrophilic organic solvent include acetone, dioxane, ethyl acetate, and aqua jojoba oil.

The hydrophobic organic solvent means an organic solvent that is not freely dissolved in water except alcohols. Examples of the hydrophobic organic solvent include an oil and fat, a silicone oil, and an ester solvent.

Examples of the oil and fat include castor oil and olive oil.

Examples of the silicone oil include dimethyl silicone oil and methylphenyl silicone oil.

Examples of the ester solvent include propylene glycol alginate, ethyl acetate, diheptyl undecyl adipate, acetylated lanolin, isostearyl glyceryl, and octyldodecyl isostearate.

The solvent included in the gel sheet of the present invention is preferably water, an alcohol, a polyhydric alcohol, a hydrophilic organic solvent, a hydrophobic organic solvent, a mixed solution of water and at least one selected from the group consisting of an alcohol, a polyhydric alcohol, an oil and fat, a silicone oil, and an ester solvent, or a mixed solution of a polyhydric alcohol and at least one selected from the group consisting of an alcohol, an oil and fat, a silicone oil, and an ester solvent. A particularly preferred solvent is water or a solution in which an alcohol or a polyhydric alcohol is dissolved in water.

For the application to a wound dressing, a system containing no alcohol is desirable because an alcohol (for example, ethanol) should not be used to wound skin. In this case, by using, as the solvent included in the gel sheet of the present invention, a solution containing one lactic acid salt selected from the group consisting of potassium lactate, sodium lactate, and calcium lactate in water, a gel sheet having sufficient strength and flexibility can be obtained.

[Other Additives Capable of Being Included]

The gel sheet of the present invention may further include, as necessary, additive components such as a physiologically active substance and a functional substance that are typically included in cosmetics, pharmaceutical products, or food. Examples of the additive include an oil base material, a moisturizer, a texture improver, a surfactant, a solvent, a propellant, an antioxidant, a stabilizer, a reducing agent, an oxidizing agent, a preservative, an antimicrobial agent, an antiseptic, a chelating agent, a pH adjuster, an acid, an alkali, powder, an inorganic salt, an ultraviolet absorber, a whitening agent, vitamins and derivatives thereof, a hair growth-promoting agent, a blood circulation-promoter, a stimulant, hormones, an anti-wrinkle agent, an anti-aging agent, a firming agent, a cooling agent, a warming agent, a wound-healing promoter, an abirritant, an analgesic, a cell activator, plant, animal, and microbial extracts, an antipruritic, a cuticle peeling and dissolving agent, an antiperspirant, a refrigerant, a styptic, an enzyme, a nucleic acid, a perfume, a coloring agent, a colorant, a dye, a pigment, an antiphlogistic, an anti-inflammatory agent, an anti-asthmatic agent, an agent for chronic obstructive pulmonary diseases, an antiallergic agent, an immunomodulator, an anti-infective agent, and an antifungal agent.

These additive components are exemplified below. Preferred examples of the oil base material include higher (polyhydric) alcohols such as cetanol, myristyl alcohol, oleyl alcohol, lauryl alcohol, cetostearyl alcohol, stearyl alcohol, arachyl alcohol, behenyl alcohol, jojoba alcohol, chimyl alcohol, selachyl alcohol, batyl alcohol, hexyldecanol, isostearyl alcohol, 2-octyldodecanol, and dimer diols; aralkyl alcohols such as benzyl alcohol and derivatives thereof; higher fatty acids such as lauric acid, myristic acid, palmitic acid, stearic acid, isostearic acid, behenic acid, undecylenic acid, 12-hydroxystearic acid, palmitoleic acid, oleic acid, linoleic acid, linolenic acid, erucic acid, docosahexaenoic acid, eicosapentaenoic acid, isohexadecanoic acid, anteiso-henicosanoic acid, a branched long-chain fatty acid, a dimer acid, and a hydrogenated dimer acid, metallic soaps thereof such as aluminum salts, calcium salts, magnesium salts, zinc salts, potassium salts, and sodium salts, and nitrogen-containing derivatives thereof such amide derivatives; hydrocarbons such as liquid paraffin (mineral oil), heavy liquid isoparaffin, light liquid isoparaffin, an α-olefin oligomer, polyisobutene, hydrogenated polyisobutene, polybutene, squalene, squalene derived from olive, squalane, vaseline, and solid paraffin; waxes such as candelilla wax, carnauba wax, rice wax, Japan wax, beeswax, montan wax, ozokerite, ceresin, paraffin wax, microcrystalline wax, petrolatum, Fischer-Tropsch Wax, polyethylene wax, and an ethylene-propylene copolymer; vegetable oils such as coconut oil, palm oil, palm kernel oil, safflower oil, olive oil, castor oil, avocado oil, sesame seed oil, tea oil, evening primrose oil, wheat germ oil, macadamia seed oil, hazelnut oil, kukui nut oil, rose hip oil, meadowfoam oil, persic oil, tea tree oil, peppermint oil, corn oil, rapeseed oil, sunflower seed oil, wheat germ oil, linseed oil, cottonseed oil, soybean oil, peanut oil, rice bran oil, cacao butter, shea butter, hydrogenated coconut oil, hydrogenated castor oil, jojoba oil, and hydrogenated jojoba oil; animal oils and fats such as beef tallow, milk fat, horse fat, egg-yolk oil, mink oil, and turtle oil; animal waxes such as spermaceti, lanolin, and orange roughy oil; lanolins such as liquid lanolin, reduced lanolin, adsorption-purified lanolin, acetylated lanolin, acetylated liquid lanolin, hydroxylated lanolin, polyoxyethylene lanolin, lanolin fatty acid, hard lanolin fatty acid, lanolin alcohol, acetylated lanolin alcohol, and acetylated (cetyl/lanolyl) ester; phospholipids such as lecithin, phosphatidylcholine, phosphatidylethanolamine, phosphatidylserine, phosphatidylglycerol, phosphatidylinositol, sphingophospholipids including sphingomyelin, phosphatidic acid, and lysolecithin; phospholipid derivatives such as hydrogenated soybean phospholipid, partially hydrogenated soybean phospholipid, hydrogenated egg yolk phospholipid, and partially hydrogenated egg yolk phospholipid; sterols such as cholesterol, dihydrocholesterol, lanosterol, dihydrolanosterol, phytosterol, and cholic acid; sapogenins; saponins; sterol esters such as cholesteryl acetate, cholesteryl nonanoate, cholesteryl stearate, cholesteryl isostearate, cholesteryl oleate, di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, an acyl sarcosine alkyl ester including isopropyl N-lauroylsarcosinate, cholesteryl 12-hydroxystearate, cholesteryl macadamiate, phytosteryl macadamiate, phytosteryl isostearate, soft lanolin fatty acid cholesteryl ester, hard lanolin fatty acid cholesteryl ester, branched long-chain fatty acid cholesteryl ester, and long chain α-hydroxy fatty acid cholesteryl ester; lipid complexes such as a phospholipid-cholesterol complex and a phospholipid-phytosterol complex; monohydric alcohol carboxylic esters such as octyldodecyl myristate, hexyldecyl myristate, octyldodecyl isostearate, cetyl palmitate, octyldodecyl palmitate, cetyl octanoate, hexyldecyl octanoate, isotridecyl isononanoate, isononyl isononanoate, octyl isononanoate, isotridecyl isononanoate, isodecyl neopentanoate, isotridecyl neopentanoate, isostearyl neopentanoate, octyldodecyl neodecanoate, oleyl oleate, octyldodecyl oleate, octyldodecyl ricinoleate, octyldodecyl lanolate, hexyldecyl dimethyloctanoate, octyldodecyl erucate, hydrogenated castor oil isostearate, ethyl oleate, ethyl avocadate, isopropyl myristate, isopropyl palmitate, octyl palmitate, isopropyl isostearate, isopropyl lanolate, diethyl sebacate, diisopropyl sebacate, dioctyl sebacate, diisopropyl adipate, dibutyloctyl sebacate, diisobutyl adipate, dioctyl succinate, and triethyl citrate; oxyacid esters such as cetyl lactate, diisostearyl malate, and hydrogenated castor oil monoisostearate; polyhydric alcohol fatty acid esters such as glyceryl trioctanoate, glyceryl trioleate, glyceryl triisostearate, glyceryl diisostearate, caprylic/capric triglyceride, caprylic/capric/myristic/stearic triglyceryl, hydrogenated rosin triglyceride (hydrogenated ester gum), rosin triglyceride (ester gum), glyceryl behenate eicosanedioate, trimethylolpropane trioctanoate, trimethylolpropane triisostearate, neopentyl glycol dioctanoate, neopentyl glycol dicaprate, 2-butyl-2-ethyl-1,3-propanediol dioctanoate, propylene glycol dioleate, pentaerythrityl tetraoctanoate, hydrogenated rosin pentaerythrityl ester, ditrimethylolpropane triethylhexanoate, ditrimethylolpropane isostearate/sebacate, pentaerythrityl triethylhexanoate, dipentaerythrityl hydroxystearate/stearate/rhodinate, diglyceryl diisostearate, polyglyceryl tetraisostearate, polyglyceryl-10 nonaisostearate, polyglyceryl-8 deca(erucate/isostearate/resinate), (hexyldecanoic acid/sebacic acid) diglyceryl oligoester, glycol distearate (ethylene glycol distearate), 3-methyl-1,5-pentanediol dineopentanoate, and 2,4-diethyl-1,5-pentanediol dineopentanoate; dimer acid derivatives or dimer diol derivatives such as diisopropyl dimer dilinoleate, diisostearyl dimer dilinoleate, di(isostearyl/phytosteryl) dimer dilinoleate, (phytosteryl/behenyl) dimer dilinoleate, (phytosteryl/isostearyl/cetyl/stearyl/behenyl) dimer dilinoleate, dimer dilinoleyl dimer dilinoleate, dimer dilinoleyl diisostearate, dirtier dilinoleyl hydrogenated rosin condensates, hydrogenated castor oil dirtier dilinoleate, and hydroxyalkyl dimer dilinoleyl ether; fatty acid alkanolamides such as coconut oil fatty acid monoethanolamide (cocamide MEA), coconut oil fatty acid diethanolamide (cocamide DEA), lauric acid monoethanolamide (lauramide MEA), lauric acid diethanolamide (lauramide DEA), lauric acid monoisopropanolamide (lauramide MIPA), palmitic acid monoethanolamide (palmitamide MEA), palmitic acid diethanolamide (palmitamide DEA), and coconut oil fatty acid methylethanolamide (cocamide methyl MEA); silicones such as dimethicone (dimethylpolysiloxane), highly-polymerized dimethicone (highly-polymerized dimethylpolysiloxane), cyclomethicone (cyclic dimethylsiloxane, decamethylcyclopentasiloxane), phenyl trimethicone, diphenyl dimethicone, phenyl dimethicone, stearoxypropyldimethylamine, a (aminoethylaminopropyl methicone/dimethicone) copolymer, dimethiconol, a dimethiconol crosspolymer, a silicone resin, a silicone rubber, an amino-modified silicone including aminopropyl dimethicone and amodimethicone, a cation-modified silicone, a polyether-modified silicone including a dimethicone copolyol, a polyglycerol-modified silicone, a sugar-modified silicone, a carboxylic acid-modified silicone, a phosphoric acid-modified silicone, a sulfuric acid-modified silicone, an alkyl-modified silicone, a fatty acid-modified silicone, an alkyl ether-modified silicone, an amino acid-modified silicone, a peptide-modified silicone, a fluorine-modified silicone, a cation-modified and polyether-modified silicone, an amino-modified and polyether-modified silicone, an alkyl-modified and polyether-modified silicone, and a polysiloxane-oxyalkylene copolymer; and fluorine oils such as perfluorodecane, perfluorooctane, and perfluoropolyether.

Preferred examples of the moisturizer and the texture improver include polyols and polymers thereof such as glycerin, 1,3-butylene glycol, propylene glycol, 3-methyl-1,3-butanediol, 1,3-propanediol, 2-methyl-1,3-propanediol, trimethylolpropane, pentaerythritol, hexylene glycol, diglycerin, polyglycerol, diethylene glycol, polyethylene dipropylene glycol, polypropylene glycol, and an ethylene glycol-propylene glycol copolymer; glycol alkyl ethers such as diethylene glycol monoethyl ether (ethoxydiglycol), ethylene glycol monoethyl ether, ethylene glycol monobutyl ether, and diethylene glycol dibutyl ether; water-soluble esters such as polyglyceryl-10 (eicosanedioate/tetradecanedioate) and polyglyceryl-10 tetradecanedioate; sugar alcohols such as sorbitol, xylitol, erythritol, mannitol, and maltitol; sugars and derivatives thereof such as glucose, fructose, galactose, mannose, threose, xylose, arabinose, fucose, ribose, deoxyribose, maltose, trehalose, lactose, raffinose, gluconic acid, glucuronic acid, cyclodextrins ($\alpha$-, $\beta$-, and $\gamma$-cyclodextrins, and modified cyclodextrins such as maltosyl cyclodextrin and hydroxyalkyl cyclodextrin), $\beta$-glucan, chitin, chitosan, heparin and derivatives thereof, pectin, arabinogalactan, dextrin, dextran, glycogen, ethyl glucoside, poly(glucosylethyl methacrylate), and a (glucosylethyl methacrylate) copolymer; hyaluronic acid and sodium hyaluronate; sodium chondroitin sulfate; mucoitin sulfate, chaoronin sulfate, kerato sulfate, and dermatan sulfate; *Tremella fuciformis* extract and *Tremella fuciformis* polysaccharides; fucoidan; tuberose polysaccharides or natural polysaccharides; organic acids such as citric acid, tartaric acid, and lactic acid and salts thereof; urea and derivatives thereof; 2-pyrrolidone-5-carboxylic acid and salts thereof including a sodium salt; amino acids such as betaine (trimethylglycine), proline, hydroxyproline, arginine, lysine, serine, glycine, alanine, phenylalanine, tyrosine, $\beta$-alanine, threonine, glutamic acid, glutamine, asparagine, aspartic acid, cysteine, cysteine, methionine, leucine, isoleucine, valine, tryptophan, histidine, and taurine and salts thereof; protein peptides and derivatives thereof such as collagen, fish collagen, atelocollagen, gelatin, elastin, peptides derived from decomposed collagen, hydrolyzed collagen, hydroxypropylammonium chloride-hydrolyzed collagen, peptides derived from decomposed elastin, peptides derived from decomposed keratin, hydrolyzed keratin, peptides derived from decomposed conchiolin, hydrolyzed conchiolin, peptides derived from decomposed silk protein, hydrolyzed silk, sodium lauroyl hydrolyzed silk, peptides derived from decomposed soy protein, peptides derived from decomposed wheat protein, hydrolyzed wheat protein, peptides derived from decomposed casein, and acylated peptides; acylated peptides such as palmitoyl oligopeptide, palmitoyl pentapeptide, and palmitoyl tetrapeptide; silylated peptides; a culture medium of lactic acid bacteria, a yeast extract solution, eggshell membrane proteins, bovine submaxillary mucin, hypotaurine, sesame lignan glycosides, glutathione, albumin, and whey; choline chloride and phosphorylcholine; and animal and plant extract components such as a placenta extract solution, elastin, collagen, aloe extract, *Hammamelis virginiana* water, *Luffa cylindrica* water, *Chamomilla recutita* extract, licorice extract, comfrey extract, silk extract, *Rosa roxburghii* extract, *Achillea millefolium* extract, *Eucalyptus globulus* extract, and melilot extract and ceramides such as natural ceramides (types 1, 2, 3, 4, 5, and 6), hydroxyceramide, pseudoceramide, sphingoglycolipid, a ceramide-containing extract, and a glucosyl-ceramide-containing extract.

Preferred examples of the surfactant include an anionic surfactant, a nonionic surfactant, a cationic surfactant, an amphoteric surfactant, and a polymer surfactant. Preferred surfactants are exemplified below. Examples of the anionic surfactant include fatty acid salts such as potassium laurate and potassium myristate; alkylsulfuric acid ester salts such as sodium lauryl sulfate, triethanolamine lauryl sulfate, and ammonium lauryl sulfate; polyoxyethylene alkylsulfates such as sodium laureth sulfate and triethanolamine laureth sulfate; acyl N-methylamino acid salts such as sodium cocoyl methyltaurate, potassium cocoyl methyltaurate, sodium lauroyl methyltaurate, sodium myristoyl methyltaurate, sodium lauroyl methylalaninate, sodium lauroyl sarcosinate, triethanolamine lauroyl sarcosinate, and sodium lauroyl glutamate methylalaninate; acyl amino acid salts such as sodium cocoyl glutamate, triethanolamine cocoyl glutamate, sodium lauroyl glutamate, sodium myristoyl glutamate, sodium stearoyl glutamate, ditriethanolamine palmitoyl aspartate, and triethanolamine cocoyl alaninate; polyoxyethylene alkyl ether acetates such as sodium laureth acetate; succinic acid ester salts such as sodium lauroyl monoethanolamide succinate; fatty acid alkanolamide ether carboxylates; acyl lactates; polyoxyethylene fatty amine sulfates; fatty acid alkanolamide sulfates; fatty acid glyceride sulfates such as glycerin hydrogenated coconut oil fatty acid sulfate sodium salt; alkylbenzene polyoxyethylene sulfates; olefin sulfonates such as sodium α-olefin sulfonate; alkyl sulfosuccinates such as disodium lauryl sulfosuccinate and sodium dioctyl sulfosuccinate; alkyl ether sulfosuccinates such as disodium laureth sulfosuccinate, sodium monolauroyl monoethanolamide polyoxyethylene sulfosuccinate, and sodium lauryl polypropylene glycol sulfosuccinate; alkylbenzene sulfonates such as sodium tetradecylbenzene sulfonate and triethanolamine tetradecylbenzene sulfonate; alkyl naphthalene sulfonates; alkane sulfonates; α-sulfofatty acid methyl ester salts; acyl isethionates; alkyl glycidyl ether sulfonates; alkyl sulfoacetate; alkyl ether phosphates such as sodium laureth phosphate, sodium dilaureth phosphate, sodium trilaureth phosphate, and sodium monoorcellinate; alkyl phosphates such as potassium lauryl phosphate; sodium caseinate; alkyl aryl ether phosphates; fatty amide ether phosphates; phospholipids such as phosphatidylglycerol, phosphatidylinositol, and phosphatidic acid; and silicone anionic surfactants such as a carboxylic acid-modified silicone, a phosphoric acid-modified silicone, and a sulfuric acid-modified silicone. Preferred examples of the nonionic surfactant include polyoxyethylene alkyl ethers having various numbers of polyoxyethylenes, such as laureths (polyoxyethylene lauryl ethers), ceteths (polyoxyethylene cetyl ethers), steareths (polyoxyethylene stearyl ethers), beheneths (polyoxyethylene behenyl ethers), isostearetths (polyoxyethylene isostearyl ethers), and octyldodeceths (polyoxyethylene octyldodecyl ethers); polyoxyethylene alkyl phenyl ethers; castor oil derivatives and hydrogenated castor oil derivatives such as polyoxyethylene hydrogenated castor oil, polyoxyethylene castor oil, polyoxyethylene hydrogenated castor oil monoisostearate, polyoxyethylene hydrogenated castor oil triisostearate, polyoxyethylene hydrogenated castor oil monopyroglutamate monoisostearate diester, and polyoxyethylene hydrogenated castor oil maleate; polyoxyethylene phytosterol; polyoxyethylene cholesterol; polyoxyethylene cholestanol; polyoxyethylene lanolin; polyoxyethylene reduced lanolin; polyoxyethylene-polyoxypropylene alkyl ethers such as polyoxyethylene-polyoxypropylene cetyl ether, polyoxyethylene-polyoxypropylene 2-decyltetradecyl ether, polyoxyethylene-polyoxypropylene monobutyl ether, polyoxyethylene-polyoxypropylene hydrogenated lanolin, and polyoxyethylene-polyoxypropylene glycerin ether; polyoxyethylene-polyoxypropylene glycol; (poly)glycerin polyoxypropylene glycols such as PPG-9 diglyceryl; glycerin fatty acid partial esters such as glyceryl stearate, glyceryl isostearate, glyceryl palmitate, glyceryl myristate, glyceryl oleate, glyceryl cocoate, glycerin mono-cottonseed oil fatty acid ester, glycerin monoerucate, glycerin sesquioleate, glycerin α,α'-oleate pyroglutamate, and glycerin monostearate malate; polyglycerin fatty acid esters such as polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, polyglyceryl-6 distearate, polyglyceryl-10 distearate, polyglyceryl-2 tristearate, polyglyceryl-10 decastearate, polyglyceryl-2 isostearate, polyglyceryl-3 isostearate, polyglyceryl-4 isostearate, polyglyceryl-5 isostearate, polyglyceryl-6 isostearate, polyglyceryl-8 isostearate, polyglyceryl-10 isostearate, polyglyceryl-2 diisostearate (diglyceryl diisostearate), polyglyceryl-3 diisostearate, polyglyceryl-10 diisostearate, polyglyceryl-2 triisostearate, polyglyceryl-2 tetraisostearate, polyglyceryl-10 decaisostearate, polyglyceryl-2 oleate, polyglyceryl-3 oleate, polyglyceryl-4 oleate, polyglyceryl-5 oleate, polyglyceryl-6 oleate, polyglyceryl-8 oleate, polyglyceryl-10 oleate, polyglyceryl-6 dioleate, polyglyceryl-2 trioleate, and polyglyceryl-10 decaoleate; ethylene glycol mono-fatty acid esters such as ethylene glycol monostearate; propylene glycol mono-fatty acid esters such as propylene glycolmonostearate; pentaerythritol fatty acid partial esters; sorbitol fatty acid partial esters; maltitol fatty acid partial esters; maltitol ether; sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, sorbitan penta-2-ethylhexylate diglycerol, and sorbitan tetra-2-ethylhexylate diglycerol; sugar derivative partial esters such as sucrose fatty acid ester, methyl glucoside fatty acid ester, and trehalose undecylenoate; alkyl glucosides such as caprylyl glucoside; alkyl polyglycosides; lanolin alcohol; reduced lanolin; polyoxyethylene fatty acid monoesters and diesters such as polyoxyethylene distearate, polyethylene glycol diisostearate, polyoxyethylene monooleate, and polyoxyethylene dioleate; polyoxyethylene-propylene glycol fatty acid esters; polyoxyethylene glycerin fatty acid esters such as polyoxyethylene monooleates including polyoxyethylene glycerin monostearate, polyoxyethylene glycerin monoisostearate, and polyoxyethylene glycerin triisostearate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monooleate, and polyoxyethylene sorbitan tetraoleate; polyoxyethylene sorbitol fatty acid esters such as polyoxyethylene sorbitol monolaurate, polyoxyethylene sorbitol monooleate, polyoxyethylene sorbitol pentaoleate, and polyoxyethylene sorbitol monostearate; polyoxyethylene methyl glucoside fatty acid esters; polyoxyethylene alkyl ether fatty acid esters; polyoxyethylene-modified animal and vegetable oils and fats such as polyoxyethylene sorbitol beeswax; alkyl glyceryl ethers such as isostearyl glyceryl ether, chimyl alcohol, selachyl alcohol, and batyl alcohol; polyhydric alcohol alkyl ethers; polyoxyethylene alkylamines; tetrapolyoxyethylene/tetrapolyoxypropylene-ethylenediamine condensates; natural surfactants such as saponin and sophorolipid; polyoxyethylene fatty amides; fatty acid alkanolamides such as coconut oil fatty acid monoethanolamide (cocamide MEA), coconut oil fatty acid diethanolamide (cocamide DEA), lauric acid monoethanolamide (lauramide MEA), lauric acid diethanolamide (lauramide DEA), lauric acid monoisopropanolamide (lauramide MIPA), palmitic acid monoethanolamide (palmitamide MEA), palmitic acid diethanolamide (palmitamide DEA), and coconut oil fatty acid methylethanolamide (cocamide methyl MEA); alkyl dimethylamine oxides such as lauramine oxide, cocamine oxide, stearamine oxide, and behenamine oxide; alkyl ethoxydimethylamine oxides; polyoxyethylene alkyl mercaptans; and silicone nonionic surfactants such as a polyether-modified silicone including a dimethicone copolyol, a polysiloxane-oxyalkylene copolymer, a polyglycerol-modified silicone, and a sugar-modified silicone. Preferred examples of the cationic surfactant include alkyl trimethylammonium chlorides such as behentrimonium chloride, steartrimonium chloride, cetrimonium chloride, and lauryltrimonium chloride; alkyl trimethylammonium bromides such as steartrimonium bromide; dialkyl dimethylammonium chlorides such as distearyldimonium chloride and dicocodimonium chloride; fatty amide amines such as stearamidopropyl dimethylamine and stearamidoethyldiethylamine and salts thereof; alkyl ether amines such as stearoxypropyldimethylamine, salts thereof, and quaternary salts thereof; fatty amide quaternary ammonium salts such as branched tong-chain fatty acid (12 to 31) aminopropylethyldimethylammonium ethyl sulfate and lanolin aminopropylethyldimethylammonium ethyl sulfate; polyoxyethylene alkylamines, salts thereof, and quaternary salts thereof; alkylamine salts; fatty amide guanidium salts; alkyl ether ammonium salts; alkyl trialkylene glycol ammonium salts; benzalkonium salts; benzethonium salts; pyridinium salts such as cetylpyridinium chloride; imidazolinium salts; alkyl isoquinolinium salts; dialkyl morpholinium salts; polyamine fatty acid derivatives; and silicone cationic surfactants such as an amino-modified silicone including aminopropyl dimethicone and amodimethicone, a cation-modified silicone, a cation-modified and polyether-modified silicone, and an amino-modified and polyether-modified silicone. Preferred examples of the amphoteric surfactant include N-alkyl-N, N-dimethylamino acid betaines such as lauryl betaine (lauryl dimethylaminoacetic acid betaine); fatty amido alkyl-N,N-dimethylamino acid betaines such as cocamide propyl betaine and lauramide propyl betaine; imidazoline-type betaines such as sodium cocoamphoacetate and sodium lauroamphoacetate; alkyl sulfobetaines such as an alkyl dimethyltaurine; sulfuric acid-type betaines such as an alkyl dimethylaminoethanol sulfate; phosphoric acid-type betaines such as an alkyl dimethylaminoethanol phosphate; phospholipids such as phosphatidylcholine, phosphatidylethanolamine, phosphatidylserine, sphingophospholipids including sphingomyelin, lysolecithin, hydrogenated soybean phospholipid, partially hydrogenated soybean phospholipid, hydrogenated egg yolk phospholipid, partially hydrogenated egg yolk phospholipid, and hydroxylated lecithin; and silicone amphoteric surfactants. Preferred examples of the polymer surfactant include polyvinyl alcohol, sodium alginate, starch derivatives, gum tragacanth, and an acrylic acid-methalkyl acrylate copolymer; and various silicone surfactants.

Preferred examples of the solvents and the propellants include lower alcohols such as ethanol, 2-propanol (isopropyl alcohol), butanol, and isobutyl alcohol; glycols such as propylene glycol, 1,3-butylene glycol, diethylene glycol, dipropylene glycol, and isopentyldiol; glycol ethers such as diethylene glycol monoethyl ether (ethoxy diglycol), ethylene glycol monoethyl ether, ethylene glycol monobutyl ether, triethylene glycol monoethyl ether, diethylene glycol diethyl ether, diethylene glycol dibutyl ether, propylene glycol monoethyl ether, and dipropylene glycol monoethyl ether; glycol ether esters such as ethylene glycol monoethyl ether acetate, diethylene glycol monoethyl ether acetate, and propylene glycol monoethyl ether acetate; glycol esters such as diethoxyethyl succinate and ethylene glycol disuccinate; benzyl alcohol, benzyloxyethanol, propylene carbonate, dialkyl carbonate, acetone, ethyl acetate, and N-methylpyrrolidone; toluene; fluorocarbons and next-generation fluorocarbon; and propellants such as LPG, dimethyl ether, and carbon dioxide gas.

Preferred examples of the antioxidant include tocopherol (vitamin E) and tocopherol derivatives such as tocopherol acetate; BHT and BHA; gallic acid derivatives such as propyl gallate; vitamin C (ascorbic acid) and/or derivatives thereof; erythorbic acid and derivatives thereof; sulfites such as sodium sulfite; hydrogen sulfites such as sodium hydrogen sulfite; thiosulfates such as sodium thiosulfate; hydrogen metasulfites; thiotaurine and hypotaurine; and thioglycerol, thiourea, thioglycolic acid, and cysteine hydrochloride.

Preferred examples of the reducing agent include thioglycolic acid, cysteine, and cysteamine.

Preferred examples of the oxidizing agent include aqueous hydrogen peroxide, ammonium persulfate, sodium bromate, and percarbonic acid.

Preferred examples of the preservative, the antimicrobial agent, and the antiseptic include hydroxybenzoic acids such as methylparaben, ethylparaben, propylparaben, and butylparaben, salts thereof, and esters thereof; salicylic acid; sodium benzoate; phenoxyethanol; 1,2-diols such as 1,2-pentanediol and 1,2-hexanediol; isothiazolinone derivatives such as methylchloroisothiazolinone and methylisothiazolinone; imidazolinium urea; dehydroacetic acid and salts thereof; phenols; halogenated bisphenols such as triclosan, acid amides thereof, and quaternary ammonium salts thereof; trichlorocarbanide, zinc pyrithione, benzalkonium chloride, benzalkonium chloride, sorbic acid, chlorhexidine, chlorhexidine gluconate, halocarban, hexachlorophene, and hinokitiol; other phenols such as phenol, isopropylphenol, cresol, thymol, p-chlorophenol, phenylphenol, and sodium phenylphenolate; and phenylethyl alcohol, photosensitive dyes, antimicrobial zeolite, and a silver ion.

Preferred examples of the chelating agent includes edetates (ethylenediamine tetraacetates) such as EDTA, EDTA-2Na, EDTA-3Na, and EDTA-4Na; hydroxyethylethylenediamine triacetates such as HEDTA-3Na; pentetates (diethylenetriamine pentaacetate); phytic acid; phosphonic acids such as etidronic acid and salts thereof including a sodium salt; sodium oxalate; polyamino acids such as polyaspartic acid and polyglutamic acid; sodium polyphosphate, sodium metaphosphate, and phosphoric acid; and sodium citrate, citric acid, alanine, dihydroxyethylglycine, gluconic acid, ascorbic acid, succinic acid, and tartaric acid.

Preferred examples of the pH adjuster, the acid, and the alkali include citric acid, sodium citrate, lactic acid, sodium lactate, potassium lactate, glycolic acid, succinic acid, acetic acid, sodium acetate, malic acid, tartaric acid, fumaric acid, phosphoric acid, hydrochloric acid, sulfuric acid, monoethanolamine, diethanolamine, triethanolamine, isopropanolamine, triisopropanolamine, 2-amino-2-methyl-1,3-propanediol, 2-amino-2-hydroxymethyl-1,3-propanediol, arginine, sodium hydroxide, potassium hydroxide, aqueous ammonia, guanidine carbonate, and ammonium carbonate.

Preferred examples of the powder include: inorganic powder having various sizes and shapes, such as mica, talc, kaolin, sericite, montmorillonite, kaolinite, mica, muscovite, phlogopite, synthetic mica, lepidolite, biotite, vermiculite, magnesium carbonate, calcium carbonate, aluminum silicate, barium silicate, calcium silicate, magnesium silicate, strontium silicate, metal tungstates, magnesium, zeolite, barium sulfate, calcined calcium sulfate, calcium phosphate, fluorapatite, hydroxyapatite, ceramic powder, bentonite, smectite, clay, mud, metallic soaps (for example, zinc myristate, calcium palmitate, and aluminum stearate), calcium carbonate, red iron oxide, yellow iron oxide, black iron oxide, ultramarine, prussian blue, carbon black, titanium oxide, titanium oxide particles and titanium oxide ultrafine particles, zinc oxide, zinc oxide particles and zinc oxide ultrafine particles, alumina, silica, fumed silica (silicic anhydride ultrafine particles), titanated mica, fish scale, boron nitride, photochromic pigments, synthetic fluorophlogopite, particulate composite powder, gold, and aluminum; inorganic powder such as hydrophobic powder or hydrophilic powder obtained by treatment of the above powder with various surface treating agents such as silicones including a hydrogen silicone and a cyclic hydrogen silicone and other silane or titanium coupling agents; and organic powder, surface-treated powder, and organic-inorganic composite powder having various sizes and shapes, such as starch, cellulose, nylon powder, polyethylene powder, polymethyl methacrylate powder, polystyrene powder, styrene-acrylic acid copolymer resin powder, polyester powder, benzoguanamine resin powder, polyethylene terephthalate-polymethyl methacrylate laminated powder, polyethylene terephthalate-aluminum-epoxy laminated powder, urethane powder, silicone powder, and Teflon (registered trademark) powder.

Preferred examples of the inorganic salts include sodium chloride-containing salts such as common salt, regular salt, rock salt, sea salt, and natural salt; potassium chloride, aluminum chloride, calcium chloride, magnesium chloride, bittern, zinc chloride, and ammonium chloride; sodium sulfate, aluminum sulfate, aluminum potassium sulfate (alum), aluminum ammonium sulfate, barium sulfate, calcium sulfate, potassium sulfate, magnesium sulfate, zinc sulfate, iron sulfate, and copper sulfate; and sodium phosphates such as mono-, di-, and tri-sodium, phosphates, potassium phosphates, calcium phosphates, and magnesium phosphates.

Preferred examples of the ultraviolet absorber include benzoate ultraviolet absorbers such as p-aminobenzoic acid, p-aminobenzoic acid monoglycerin ester, N,N-dipropoxy-p-aminobenzoic acid ethyl ester, N,N-diethoxy-p-aminobenzoic acid ethyl ester, N,N-dimethyl-p-aminobenzoic acid ethyl ester, N,N-dimethyl-p-aminobenzoic acid butyl ester, and N,N-dimethyl-p-aminobenzoic acid ethyl ester; anthranilate ultraviolet absorbers such as homomethyl-N-acetylanthranilate; salicylate ultraviolet absorbers such as salicylic acid and a sodium salt thereof, amyl salicylate, menthy salicylate, homomenthyl salicylate, octyl salicylate, phenyl salicylate, benzyl salicylate, and p-isopropanolphenyl salicylate; cinnamate ultraviolet absorbers such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, 2-ethylhexyl p-methoxycinnamate (p-methoxycinnamic acid octyl ester), 2-ethoxyethyl p-methoxycinnamate (cinoxate), cyclohexyl p-methoxycinnamate, ethyl α-cyano-α-phenylcinnamate, 2-ethylhexyl α-cyano-β-phenylcinnamate (octocrylene), glyceryl mono-2-ethylhexanoyl di-p-methoxycinnamate, ferulic acid, and derivatives thereof; benzophenone ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone (oxybenzone-3), 2-hydroxyphenone 5-sulfonate, 4-phenylbenzophenone, 2-ethylhexyl-4"-phenyl-benzophenone 2-carboxylate, 2-hydroxy-4-n-octoxybenzophenone, and 4-hydroxy-3-carboxybenzophenone; 3-(4'-methylbenzylidene)-d,l-camphor and 3-benzylidene-d,l-camphor; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methyl-phenylbenzotriazole; dibenzalazine; dianisoyltmethane; 5-(3,3-dimethyl-2-norbornylidene)-3-pentan-2-one; dibenzoylmethane derivatives such as 4-t-butylmethoxydibenzoylmethane; octyl triazone; urocanic acid and urocanic acid derivatives such as ethyl urocanate; and 2-(2'-hydroxy-5'-methylphenyl) benzotriazole, 1-(3,4-dimethoxyphenyl)-4,4-dimethyl-1,3-pentanedione, hydantoin derivatives such as 2-ethylhexyl dimethoxybenzylidene dioxoimidazolidine propionate, phenylbenzimidazole sulfonic acid, terephthalylidene dicamphor sulfonic add, drometrizole trisiloxane, methyl anthranilate, rutin and derivatives thereof, and oryzanol and derivatives thereof.

Preferred examples of the whitening agent include hydroquinone glycosides such as arbutin and α-arbutin and esters thereof; ascorbic acid and ascorbic acid derivatives such as an ascorbyl phosphate salt including sodium ascorbyl phosphate and magnesium ascorbyl phosphate, an ascorbic acid fatty acid ester including ascorbic acid tetraisopalmitate, an ascorbic acid alkyl ether including ascorbic acid ethyl ether, an ascorbic acid glucoside including ascorbic acid 2-glucoside and fatty acid esters thereof, ascorbyl sulfate, and tocopheryl ascorbyl phosphate; and kojic acid, ellagic acid, tranexamic acid and derivatives thereof, ferulic acid and derivatives thereof, placenta extract, glutathione, oryzanol, butylresoreinol, and plant extracts such as oil-soluble *Chamomilla recutita* extract, oil-soluble licorice extract, *Tamarix chinensis* extract, and saxifrage extract.

Preferred examples of the vitamins and derivatives thereof include vitamins A such as retinol, retinol acetate, and retinol palmitate; vitamins Bs such as thiamine hydrochloride, thiamine sulfate, riboflavin, riboflavin acetate, pyridoxine hydrochloride, pyridoxine dioctanoate, pyridoxine dipalmitate, flavin adenine dinucleotide, cyanocobalamin, folic acids, nicotinic acids including nicotinamide and benzyl nicotinate, and cholines; vitamins C such as ascorbic acid and salts thereof including a sodium salt; vitamins D; vitamins E such as α, β, γ, and δ-tocopherols; other vitamins such as pantothenic acid and biotin; ascorbic acid derivatives such as an ascorbyl phosphate salt including sodium ascorbyl phosphate and magnesium ascorbyl phosphate, an ascorbyl fatty acid ester including ascorbyl tetraisopalmitate, ascorbyl stearate, ascorbyl palmitate, and ascorbyl dipalmitate, an ascorbic acid alkyl ether including ascorbic acid ethyl ether, an ascorbic acid glucoside including ascorbic acid 2-glucoside and fatty acid esters thereof, and an ascorbic acid derivative such as tocopheryl ascorbyl phosphate; tocopherol derivatives such as tocopherol nicotinate, tocopherol acetate, tocopherol linoleate, tocopherol ferulate, and tocopherol phosphate, tocotrienol, and other various vitamin derivatives.

Preferred examples of the hair growth-promoting agent, the blood circulation-promoter, and the stimulant include plant extracts and tinctures such as swertia herb extract, capsicum tincture, ginger tincture, ginger extract, and cantharis tincture; and capsaicin, nonylic acid vanillylamide, zingerone, ichthammol, tannic acid, borneol, cyclandelate, cinnarizine, tolazoline, acetylcholine, verapamil, cepharanthine, γ-oryzanol, cepharanthine, vitamin E and derivatives thereof including tocopherol nicotinate and tocopherol acetate, γ-oryzanol, nicotinic acid and derivatives thereof including nicotinamide, benzyl nicotinate, inositol hexanicotinate, and nicotinic alcohol, allantoin, Kankoso 301, Kankoso 401, carpronium chloride, pentadecanoic acid monoglyceride, flavanonol derivatives, stigmasterol and stigmastanol and glycosides thereof, and minoxidil Preferred examples of the hormones include estradiol, estrone, ethynylestradiol, cortisone, hydrocortisone, and prednisone.

Preferred examples of other medical agents such as the anti-wrinkle agent, the anti-aging agent, the firming agent, the cooling agent, the warming agent, the wound-healing promoter, the abirritant, the analgesic, and the cell activator include retinols, retinoic acids, and tocopheryl retinoate;

lactic acid, glycolic acid, gluconic acid, fruit acid, salicylic acid and derivatives thereof such as glycosides and esters thereof, and α- or β-hydroxy acids and derivatives thereof such as hydroxycapric acid, a long chain α-hydroxy fatty acid, and a long chain α-hydroxy fatty acid cholesteryl ester; γ-aminobutyric acid and γ-amino-β-hydroxybutyric acid; carnitine; carnosine; creatine; ceramides and sphingosines; anti-oxidizing agents and active oxygen scavengers such as caffeine, xanthine, and other substances and derivatives thereof; coenzyme Q10, carotene, lycopene, astaxanthin, lutein, α-lipoic acid, colloidal platinum nanoparticles, and fullerenes; catechins; flavones such as quercetin; isoflavones; gallic acid and sugar ester derivatives thereof; polyphenols such as tannin, sesamin, proanthocyanidin, chlorogenic acid, and apple polyphenols; rutin and derivatives thereof such as a glycoside thereof; hesperidin and derivatives thereof such as a glycoside thereof; lignan glycosides; licorice extract related substances such as glabridin, glabrene, liquiritin, and isoliquiritin; lactoferrin; shogaol and gingerol; perfume substances such as menthol and cedrol and derivatives thereof; capsaicin, vanillin, and other substances and derivative thereof; insect repellents such as diethyltoluamide; and complexes of a physiologically active substance and cyclodextrins.

Preferred examples of the plant, animal, and microbial extracts include iris extract, *Angelica keiskei* extract, *Thujopsis dolabrata* extract, asparagus extract, avocado extract, *Hydrangea serrata* extract, almond extract, *Althaea officinalis* extract, *Arnica montana* extract, aloe extract, apricot extract, apricot kernel extract, ginkgo extract, *Artemisia capillaris* flower extract, fennel seed extract, turmeric root extract, oolong tea extract, uva-ursi extract, rose fruit extract, *Echinacea angustifolia* leaf extract, *Isodonis japonicus* extract, scutellaria root extract, phellodendron bark extract, coptis rhizome extract, barley extract, *Panax ginseng* extract, hypericum extract, *Lamium album* extract, *Ononis spinosa* extract, *Nasturtium officinale* extract, orange extract, dried sea water residues, seaweed extract, Japanese persimmon leaf extract, *Pyracantha fortuneana* extract, hydrolyzed elastin, hydrolyzed wheat powder, hydrolyzed silk, pueraria root extract, *Chamomilla recutita* extract, oil-soluble *Chamomilla recutita* extract, carrot extract, *Artemisia capillaris* extract, *Avena fatua* extract, *Hibiscus sabdariffa* extract, licorice extract, oil-soluble licorice extract, kiwi fruit extract, kiou extract, jew's-ear extract, cinchona extract, cucumber extract, *Paulownia tomentosa* leaf extract, guanosine, guava extract, *sophora* root extract, *Gardenia jasminoides* extract, *Sasa veitchii* extract, *Sophora flavescens* extract, walnut extract, chestnut extract, grapefruit extract, *Clematis vitalba* extract, black rice extract, black sugar extract, black vinegar, chlorella extract, mulberry extract, gentian extract, geranium herb extract, black tea extract, yeast extract, magnolia bark extract, coffee extract, burdock root extract, rice extract, fermented rice extract, fermented rice bran extract, rice germ oil, comfrey extract, collagen, bilberry extract, asiasarum root extract, bupleurum root extract, umbilical cord extract solution, saffron extract, salvia extract, *Saponaria officinalis* extract, bamboo grass extract, *Crataegus cuneata* extract, *Bombyx mori* excrementum extract, zanthoxylum fruit extract, shiitake mushroom extract, rehmannia root extract, lithospermum root extract, *Perilla frutescens* extract. *Tilia japonica* extract, *Filipendula multijuga* extract, jatoba extract, peony root extract, ginger extract, *Acorus calamus* root extract, *Betula alba* extract, *Tremella fuciformis* extract, *Equisetum arvense* extract, stevia extract, stevia fermentation product, *Tamarix chinensis* extract, *Hedera helix* extract, *Crataegus oxycantha* extract, *Sambucus nigra* extract, *Achillea millefolium* extract, *Mentha piperita* extract, sage extract, mallow extract, cnidium rhizome extract, swertia herb extract, mulberry bark extract, rhubarb extract, soybean extract, jujubi extract, thyme extract, dandelion extract, lichens extract, tea extract, clove extract, *Imperata cylindrica* extract, citrus unshiu peel extract, tea tree oil, *Rubus suavissimus* extract, capsicum extract, Japanese *angelica* root extract, *Calendula officinalis* extract, peach kernel extract, bitter orange peel extract, *Houttuynia cordata* extract, tomato extract, natto extract, carrot extract, garlic extract, *Rosa multiflora* extract, *hibiscus* extract, ophiopogon tuber extract, lotus extract, parsley extract, birch extract, honey, *Hamamelis virginiana* extract, *Parietaria officinalis* extract, *Rabdosia japonica* extract, bisabolol, Japanese cypress extract, *Bifidobacterium* extract, loquat extract, coltsfoot extract, Japanese butterbur flower-bud extract, hoelen extract, *Ruscus aculeatus* extract, grape extract, grape seed extract, propolis, *Luffa cylindrica* extract, safflower extract, peppermint extract, *Tilia miqueliaria* extract, *Paeonia suffruticosa* extract, hop extract, *Rosa rugosa* extract, pine extract, *Aesculus hippocastanum* extract, *Lysichiton camtschatcense* extract, *Sapindus mukurossi* extract, *Melissa officinalis* extract, *Nemacystus decipiens* extract, peach extract, cornflower extract, *Eucalyptus globulus* extract, saxifrage extract, *Citrus junos* extract, lily extract, coix seed extract, *Artemisia princeps* extract, lavender extract, green tea extract, egg shell membrane extract, apple extract, rooibos tea extract, *Litchi chinensis* extract, lettuce extract, lemon extract, forsythia fruit extract, *Astragalus sinicus* extract, rose extract, rosemary extract, *Anthemis nobilis* extract, royal jelly extract, and burnt extract.

Examples of the antipruritic include diphenhydramine hydrochloride, chlorpheniramine maleate, camphor, and a substance P inhibitor.

Examples of the cuticle peeling and dissolving agent include salicylic acid, sulfur, resorcin, selenium sulfide, and pyridoxine.

Examples of the antiperspirant include aluminum chlorohydrate, aluminum chloride, zinc oxide, and zinc p-phenolsulfonate.

Examples of the refrigerant include menthol and methyl salicylate.

Examples of the styptic include citric acid, tartaric acid, lactic acid, aluminum potassium sulfate, and tannic acid.

Examples of the enzymes include superoxide dismutase, catalase, lysozyme chloride, lipase, papain, pancreatin, and protease.

Preferred examples of the nucleic acids include ribonucleic acids and salts thereof, deoxyribonucleic acids and salts thereof, and adenosine triphosphate disodium.

Preferred examples of the perfume include synthetic perfumes and natural perfumes such as acetyl cedrene, amylcinnamaldehyde, allylamyl glycolate, β-ionone, Iso E Super, isobutylquinoline, iris oil, irone, indole, ylang-ylang oil, undecanal, undecenal, γ-undecalactone, estragole, eugenol, oakmoss, opoponax resinoid, orange oil, eugenol, aurantiol, galaxolide, carvacrol, L-carvone, camphor, canon, carrot seed oil, clove oil, methyl cinnamate, geraniol, geranyl nitrile, isobornyl acetate, geranyl acetate, dimethylbenzylcarbinyl acetate, styralyl acetate, cedryl acetate, terpinyl acetate, p-t-butylcyclohexyl acetate, vetiveryl acetate, benzyl acetate, linalyl acetate, isopentyl salicylate, benzyl salicylate, sandalwood oil, santalol, cyclamen aldehyde, cyclopentadecanolide, methyl dihydrojasmonate, dihydromyrcenol, jasmine absolute, jasmine lactone, cis-jasmone, citral, citronellol, citronellal, cinnamon bark oil, 1,8-cineole, cinnamaldehyde, styrax resinoid, cedarwood oil, cedrene, cedrol, celery seed oil, thyme oil, damascone, damascenone, thymol, tuberose absolute, decanal, decalactone, terpineol, 7-terpinen, triplal, nerol, nonanal, 2,6-nonadienal, nonalactone, patchouli alcohol, vanilla absolute, vanillin, basil oil, patchouli oil, hydroxycitronclial, α-pinene, piperitone, phenethyl alcohol, phenylacetaldehyde, petitgrain oil, hexylcinnamaldehyde, cis-3-hexenol, Peru balsam, vetiver oil, vetiverol, peppermint oil, pepper oil, heliotropin, bergamot oil, benzyl benzoate, borneol, mil resinoid, musk ketone, methylnonylacetaldehyde, γ-methylionone, menthol, L-menthol, L-menthone, *Eucalyptus globulus* oil, β-ionone, lime oil, lavender oil, D-limonene, linalool, lyral, filial, lemon oil, rose absolute, rose oxide, rose oil, rosemary oil, and various essential oils and various perfume blends.

Preferred examples of the coloring agent, the colorant, the dye, and the pigment include legal colors such as Brown No. 201, Black No. 401, Violet No. 201, Violet No. 401, Blue No. 1, Blue No. 2, Blue No. 201, Blue No. 202, Blue No. 203, Blue No. 204, Blue No. 205, Blue No. 403, Blue No. 404, Green No. 201, Green No. 202, Green. No. 204, Green No. 205, Green No. 3, Green No. 401, Green No. 402, Red No. 102, Red No. 104-1, Red No. 105-1, Red No. 106, Red No. 2, Red No. 201, Red No. 202, Red No. 203, Red No. 204, Red No. 205, Red No. 206, Red No. 207, Red No. 208, Red No. 213, Red No. 214, Red No. 215, Red No. 218, Red No. 219, Red No. 220, Red No. 221, Red No. 223, Red No. 225, Red No. 226, Red No. 227, Red No. 228, Red No. 230-1, Red No. 230-2, Red No. 231, Red No. 232, Red No. 3, Red No. 401, Red No. 404, Red No. 405, Red No. 501, Red No. 502, Red No. 503, Red No. 504, Red No. 505, Red No. 506, Orange No. 201, Orange No. 203, Orange No. 204, Orange No. 205, Orange No. 206, Orange No. 207, Orange No. 401, Orange No. 402, Orange No. 403, Yellow No. 201, Yellow No. 202-1, Yellow No. 202-2, Yellow No. 203, Yellow No. 204, Yellow No. 205, Yellow No. 4, Yellow No. 401, Yellow No. 402, Yellow No. 403-1, Yellow No. 404, Yellow No. 405, Yellow No. 406, Yellow No. 407, and Yellow No. 5; other acid dyes such as Acid Red No. 14; basic dyes such as Arianor Sienna Brown, Arianor Madder Red, Arianor Steel Blue, and Arianor Straw Yellow; nitro dyes such as HC Yellow No. 2, HC Yellow No. 5, HC Red No. 3,4-hydroxypropylamino-3-nitrophenol, N,N'-bis(2-hydroxyethyl)-2-nitro-p-phenylenediamine, HC Blue No. 2, and Basic Blue No. 26; disperse dyes; inorganic white pigments such as titanium dioxide and zinc oxide; inorganic red pigments such as iron oxide (red iron oxide) and iron titanate; inorganic brown pigments such as γ-iron oxide; inorganic yellow pigments such as yellow iron oxide and ocher; inorganic black pigments such as black iron oxide and low-order titanium oxide; inorganic violet pigments such as mango violet and cobalt violet; inorganic green pigments such as chromium oxide, chromium hydroxide, and cobalt titanate; inorganic blue pigments such as ultramarine and prussian blue; pearl pigments such as titanium oxide-coated mica, titanium oxide-coated bismuth oxychloride, titanium oxide-coated talc, colored titanium oxide-coated mica, bismuth oxychloride, and fish scale; metal powder pigments such as aluminum powder, copper powder, and gold; surface treated inorganic and metal powder pigments; organic pigments such as zirconium lake, barium lake, and aluminum lake; surface treated organic pigments; natural coloring agents and dyes such as anthraquinones including astaxanthin and alizarin, naphthoquinones including anthocyanidin, β-carotene, catenal, capsanthin, chalcone, carthamin, quercetin, crocin, chlorophyll, curcumin, cochineal, and shikonin, bixin, flavones, betacyanidine, henna, hemoglobin, lycopene, riboflavin, and rutin; oxidation dye intermediates and couplers such as p-phenylenediamine, toluene-2, 5-diamine, o-, m-, and p-aminophenols, m-phenylenediamine, 5-amino-2-methylphenol, resorcin, 1-naphthol, and 2,6-diaminopyridine and salts thereof; autoxidizable dyes such as indoline; and dihydroxyacetone.

Preferred examples of the antiphlogistics and the anti-inflammatory agent include glycyrrhizic acid and derivatives thereof, glycyrrhetic acid derivatives, salicylic acid derivatives, hinokitiol, guaiazulene, allantoin, indomethacin, ketoprofen, felbinac, ibuprofen, diclofenac, loxoprofen, celecoxib, infliximab, etanercept, zinc oxide, hydrocortisone acetate, prednisone, diphenhydramine hydrochloride, and chlorpheniramine maleate; and plant extracts such as peach leaf extract and *Artemisia princeps* leaf extract.

Preferred examples of the anti-asthmatic agent, the agent for chronic obstructive pulmonary diseases, the antiallergic agent, and the immunomodulator include aminophylline, theophyllines, steroids (such as flutieasone and beclomethasone), leukotriene antagonists, thromboxane inhibitors, Intal, β2 agonists (such as formoterol, salmeterol, albuterol, tulobuterol, clenbuterol, and epinephrine), tiotropium, ipratropium, dextromethorphan, dimemorfan, bromhexine, tranilast, ketotifen, azelastine, cetirizine, chlorpheniramine, mequitazine, tacrolimus, ciclosporin, sirolimus, methotrexate, cytokine modulators, interferon, omalizumab, and proteins/antibodies.

Preferred examples of the anti-infective agent and the antifungal agent include oseltamivir, zanamivir, and itraconazole.

In addition to these components, the gel sheet of the present invention may include known cosmetics ingredients, known pharmaceutical ingredients, known food ingredients, and others such as ingredients described in The Japanese Standards of Cosmetic Ingredients, Japanese Cosmetic Ingredients Codex, Japanese Cosmetic Labeling Name list issued by Japan Cosmetic Industry Association, INCI dictionary (The International Cosmetic Ingredient Dictionary and Handbook), Japanese Standards of Quasi-drag Ingredients, Japanese Pharmacopoeia, Japanese Pharmaceutical Excipients, Japan's Specifications and Standards for Food Additives, and other standards and ingredients described in Japanese and foreign patent publications and patent application Publications (including Japanese Translations of PCT International applications and Domestic Re-Publications of PCT International applications) categorized as International Patent Classification IPC of A61K7 and A61K8, in a known combination and in a known formulation ratio or a known formulation amount.

The gel sheet of the present invention obtained as above can be used for a skin care product, a cosmetic base material, a beauty base material, a clean product, an external preparation, a base material for pharmaceutical products, a quasi-drug, a wound dressing, an antiadhesive film, a drug delivery system, a cell culture base material, a regenerative medicine base material, an air freshener, a deodorant, an insect repellent, an insecticide, a base material for agrochemicals, a base material for diagnosis agents, a solving material for chemical reaction or enzyme reaction, a base material for chemical sensors, a base material for biosensors, food, and other purposes and is particularly preferably expected to be applied as wound dressings such as a wound dressing sheet.

For preparing the gel sheet of the present invention, first, the lipid peptide gelator, the polymeric compound, if desired, a solvent such as water and an alcohol, and other additives such as a physiologically active substance and a functional substance are mixed and then, if desired, the mixture is heated and stirred, and left, thereby affording an amorphous gel or sol.

The obtained gel or sol is dropped on a smooth surface or is poured in an appropriate mold in an appropriate amount, for example, and then is left thr an appropriate period of time or then is subjected to a freezing and thawing process. This allows the gel or sol to be solidified into a sheet (film) shape, thereby affording the gel sheet of the present invention.

Alternatively, the obtained amorphous gel may be extruded with a syringe or other means and then be rapidly cooled. This allows the gel to be solidified into a fiber shape or a spherical shape.

The gel sheet may be combined with a nonwoven fabric, a film, or a foam that is a support medium laminated on the sheet to form a laminate, thereby achieving what is called an adhesive patch. The laminate may further include a release film laminated on the opposite surface of the sheet to the support medium.

In such a case, the support medium may be any support medium commonly used for adhesive patches and is preferably selected from polyurethane, PVA, polypropylene, and a laminated support medium of these, for example.

The laminate obtained in this manner can be suitably used for a wound dressing as with the gel sheet.

Figure 7:
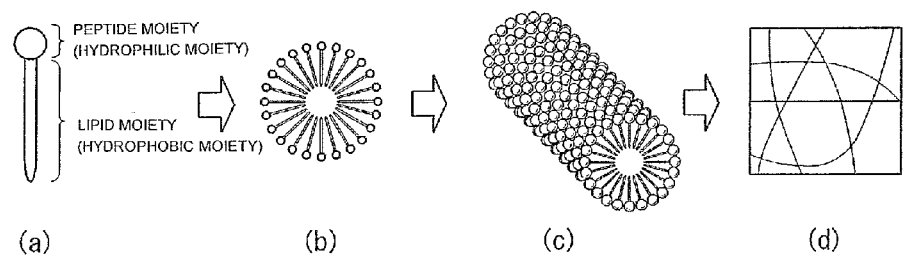
FIG. 7 is a schematic diagram of the self-assembling and gelation of a lipid peptide gelator in water, an alcohol, a polyhydric alcohol, and a hydrophilic organic solvent.
Figure 9:
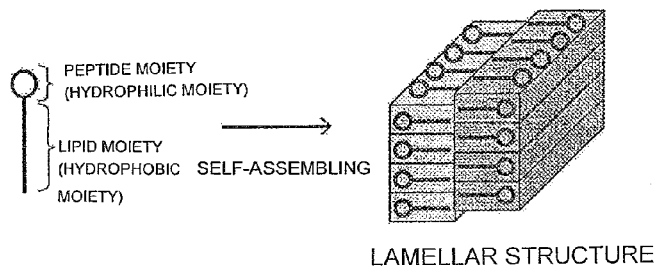
FIG. 9 is a schematic diagram of the self-assembling (lamellar secondary assembly) of the lipid peptide gelator in an alcohol, a polyhydric alcohol, and a hydrophilic organic solvent.

If the lipid peptide gelator including the lipid peptide of Formula (1) or a pharmaceutically usable salt of the lipid peptide used in the present invention is put into water, an alcohol, a polyhydric alcohol, or a hydrophilic organic solvent, the peptide moieties in Formula (1) form intermolecular noncovalent bonds through hydrogen bonds to each other, and the lipid moieties in Formula (1) are hydrophobically packed to be self-assembled, thus forming a tubular secondary assembly, that is, a fiber, as shown in FIG. 7 or forming a lamellar secondary assembly as shown in FIG. 9.

For reference, FIG. 7 shows a schematic diagram exemplifying the self-assembling and gelation of lipid peptides used as the gelator in water, an alcohol, a polyhydric alcohol, or a hydrophilic organic solvent (in the present invention, not all of the lipid peptides form the self-assembly and gel shown in FIG. 7). The lipid peptides (a) are assembled while placing those lipid moieties as the hydrophobic moiety at the center (b), and then are self-assembled to form a fiber (c).

If the fiber is formed in the hydrophilic liquid such as water, the fibers form a three-dimensional network structure (for example, see FIG. 7D). Then, the peptide moieties on the fiber surface form bonds to the hydrophilic liquid. This swells the network structure to cause the gelation of the whole hydrophilic liquid.

If the lipid peptide gelator of the present invention is put into a hydrophobic organic solvent, the lipid peptides are self-assembled while placing those peptide moieties in Formula (1) at the center and placing those lipid moieties on the surface layer, thus forming a tubular secondary assembly, that is, a fiber.

Figure 8:
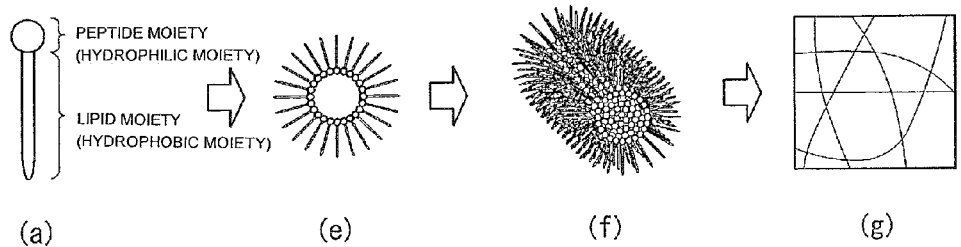
FIG. 8 is a schematic diagram of the self-assembling and gelation of the lipid peptide gelator in a hydrophobic organic solvent.

For reference, FIG. 8 shows a schematic diagram exemplifying the self-assembling and gelation of lipid peptides in a hydrophobic organic solvent (in the present invention, not all of the lipid peptides form the self-assembly and gel shown in FIG. 8). The lipid peptide molecules (a) are assembled while placing histidine moieties as the hydrophilic moiety at the center (e), and then are self-assembled to form a fiber (f). If the fibers are formed in a hydrophobic organic solvent, the fibers form a three-dimensional network structure (for example, see FIG. 2G). Then, the lipid moieties on the fiber surface form bonds to the hydrophobic organic solvent. This swells the network structure to cause the gelation of the whole hydrophobic organic solvent.

Although the detailed mechanism during the formation of the (amorphous) gel constituting the gel sheet of the present invention has not been revealed, the charge state of the lipid peptide is supposed to contribute.

The lipid peptide used as the gelator in the present invention is a zwitterionic compound having a carboxy group at the C terminal and an amino group derived from the side chain —$(CH_2)n$-X group of the peptide moiety. The compound includes an ionic state in which only the carboxy group is anionized, an ionic state in which only the amino group is cationized, an ionic state in which both the groups are charged (zwitterionic state), and an ionic state in which neither substituent is charged, and those four ionic states are supposed to be in equilibrium.

In view of the acid dissociation constant of an amino acid residue, the lipid peptide molecule is assumed to include the following states. In an acidic region, the terminal amino group derived from the —$(CH_2)n$-X group of the peptide moiety is positively charged, and the lipid peptide molecule is cationized. In a basic region, the terminal carboxy group at the C terminal is negatively charged, and the lipid peptide molecule is anionized. In a neutral region, the zwitterionic state is mainly present.

An ionized lipid peptide molecule has a peptide moiety having increased affinity with water. Such lipid peptide molecules are self-assembled so that the long chain moiety as the hydrophobic moiety is not in contact with water, thus forming a nanofiber. At that time, when the zwitterionic state is mainly present, a positive ion of one nanofiber is ionically bonded to a negative ion of another nanofiber, and the resulting ionic bonds form a cross-linked network structure. The formation of the network structure enables the network structure to incorporate water in a larger amount, and this is believed to be the reason why the lipid peptide molecule achieves excellent hydrogel formability.

Although the detailed formation mechanism of the gel sheet of the present invention has been also unclear, an assumed mechanism is as below. Noncovalent bonds that serve as a driving force for the gelation of a low molecular weight compound, such as a hydrogen bond, van der Waals force, π-π interaction, and electrostatic interaction, cause, in the presence of a polymeric compound, noncovalently, strong intermolecular interaction to the polymeric compound. This interaction between the molecules allows molecule assembly processes of a low molecular weight compound, that is, the formation of a fibrous assembly, the formation of a three-dimensional structure, and the stabilization of a gel to proceed, thereby forming the (amorphous) gel.

For example, when a polyvinyl alcohol solution is alternately subjected to a condition at a freezing point or low and a condition at a freezing point or higher by freezing and thawing, respectively, a cross-linked hydrogen bond of OH groups is formed. The hydrogen bond interaction between the low molecular weight compound of the present invention and the polyvinyl alcohol is assumed to greatly accelerate the fiber formation and the gel formation. This huge bonding effect is supposed to enable the gel to incorporate water in a highly efficient manner, thereby enabling the formation of the gel sheet having a novel feel in use of the present invention.

Hence, it is believed that the mechanism presented above causes a huge interaction between the fibrous structure of the low molecular weight compound and the network of the polymeric compound and this surprisingly leads to the formation of the fixed gel (gel sheet).

EXAMPLES

The present invention will now be described in detail with reference to Examples and Test Examples, but the present invention is not limited to these Examples.

Abbreviations used in Examples mean the following compounds.
Gly: glycine
His: histidine
PVA: polyvinyl alcohol Synthesis Example 1

Synthesis of Lipid Peptide (N-Palmitoyl-Gly-His)

The lipid peptide used in Examples was synthesized in accordance with the method shown below.

Into a 4-necked 500-mL flask, 14.2 g (91.6 mmol) of histidine, 30.0 g (91.6 mmol) of N-palmitoyl-Gly-methyl, and 300 g of toluene were charged, and 35.3 g (183.2 mmol) of 28% sodium methoxide methanol solution was added as a base. The whole was heated in an oil bath at 60° C. and stirred for 1 hour. Then, the oil bath was removed, and the solution was allowed to cool to 25° C. To the solution, 600 g of acetone was added, and the product was reprecipitated and filtered. The solid obtained here was dissolved in a mixed solution of 600 g of water and 750 g of methanol. To the solution, 30.5 (183.2 mmol) of 6N hydrochloric acid was added to neutralize the solution, and the precipitated solid was filtered. Next, the obtained solid was dissolved in a mixed solution of 120 g of tetrahydrofuran and 30 g of water at 60° C., and 150 g of ethyl acetate was added. The solution was cooled from 60° C. to 30° C. Then, the precipitated solid was filtered. The obtained solid was dissolved in a mixed solvent of 120 g of tetrahydrofuran and 60 g of acetonitrile. The solution was heated to 60° C., then stirred for 1 hour, and cooled, followed by filtration. The obtained solid was washed with 120 g of water, filtered, and then was dried under reduced pressure to afford 26.9 g of white crystal of free N-palmitoyl-Gly-His (hereinafter also simply called N-palmitoyl-Gly-His) (yield 65%).

Example 1

Preparation of Gel Sheet

N-Palmitoyl-Gly-His synthesized above was dissolved in a 50 mM phosphate buffer solution (pH 7.5) so as to give a concentration of 1% (w/w) in a closed system at 100° C. To the solution, gum arable (Wako Pure Chemical Industries, Ltd.) was added dropwise so as to give a concentration of 10% (w/w) so as to form gel. From the formed gel, 200 µl of the gel was taken and dropped onto a glass petri dish. The gel was left overnight and then observed. To the gel after standing overnight, milliQ water was dropped, and the affinity with water was observed. Also, PVA (manufactured by Wako Pure Chemical Industries, Ltd., n=1,500 to 1,800) at a concentration of 10% (w/w) was added dropwise, in place of the gum arabic, so as to form gel. Then, the gel was subjected to the same procedure, and the gel after standing overnight was observed.

For comparison, gum arable alone or PVA alone was used without using N-palmitoyl-Gly-His and was dropped onto a glass petri dish in a similar manner. Then, each sample was left overnight and then observed in a similar manner.

From the observation results, a sample ascertained to have the affinity with water is evaluated as ○, and a sample ascertained to have no affinity with water is evaluated as x. Table 1 shows the results.

Figure 2:
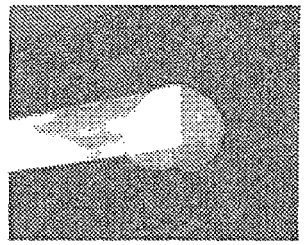
FIG. 2 is a magnified photograph of a gel sheet that contained N-palmitoyl-Gly-His and gum arabic and was left overnight.
Figure 3:
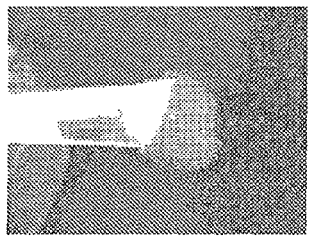
FIG. 3 is a magnified photograph of a gel sheet that contained N-palmitoyl-Gly-His and PVA and was left overnight.

FIG. 1 shows photographs of the samples that were dropped on a glass petri dish and were left overnight (the result in Table 1 with photographs), FIG. 2 shows a magnified photograph of the sample of N-palmitoyl-Gly-His and gum arabic after standing overnight, and FIG. 3 shows a magnified photograph of the sample of N-palmitoyl-Gly-His and PVA after standing overnight.

Figure 4:
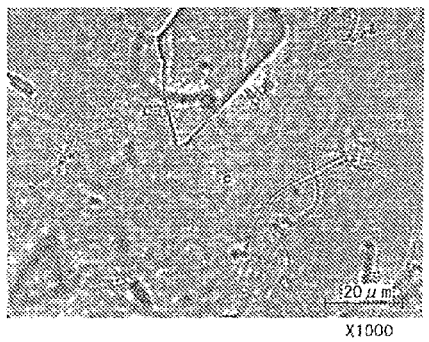
FIG. 4 is a photograph of a gel sheet that contained N-palmitoyl-Gly-His and gum arabic, was left overnight, and was observed under an optical microscope.
Figure 5:
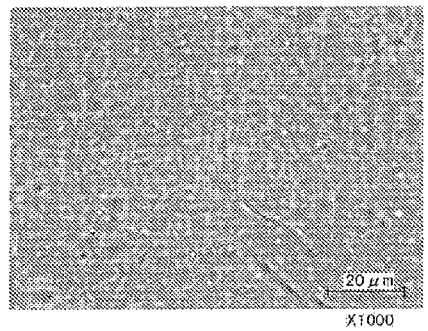
FIG. 5 is a photograph of a gel sheet that contained N-palmitoyl-Gly-His and PVA, was left overnight, and was observed under an optical microscope.

FIG. 4 (gum arabic) and FIG. 5 (PVA) show photographs of respective gels after standing overnight observed under an optical microscope.

TABLE 1

Change in gel state after standing overnight

|  | milliQ | Gum arabic | PVA |
|---|---|---|---|
| Without N-palmitoyl-Gly-His | — | Low viscosity Cloudy due to particles | High viscosity |
| With N-palmitoyl-Gly-His | White gel formed | White gel formed Gel sheet formed | Slightly white gel formed Gel sheet formed |
| Affinity with water by addition of milliQ water | ○ | ○ | x |

As shown in Table 1 and FIG. 1 to FIG. 3, a blend system of N-palmitoyl-Gly-His and gum arabic or the blend system of N-palmitoyl-Gly-His and PVA is ascertained to form a sheet-like gel (hereinafter called a gel sheet) after standing overnight.

The gel sheet formed of N-palmitoyl-Gly-His and gum arabic had stretch properties, and the dried film (sheet) had a small thickness and were rich in water to show hydrophilicity.

In contrast, the gel sheet formed of N-palmitoyl-Gly-His and PVA had high elasticity, and the film (sheet) was dry and had low hydrophilicity (affinity with water by addition of milliQ water), a relatively large thickness, and a shrunk edge.

Each gel sheet failed to be rich in water into an (amorphous) gel after the addition of milliQ water, and the result revealed that the film (sheet) had low water absorbability.

As shown in FIG. 4 and FIG. 5, the formation of a fibrous structure derived from N-palmitoyl-Gly-His was observed in the gel sheet formed of N-palmitoyl-Gly-His and gum arabic or PVA.

Example 2, Example 3, and Comparative Examples 1 to Comparative Example 3

Preparation of Gel Sheet by Freezing-Thawing Method (1)

Each of N-palmitoyl-Gly-His synthesized above, PVA (manufactured by Kuraray Co., Ltd.), and pure water (manufactured by Kyoei Pharmaceutical Industries, Ltd., Japanese Pharmacopoeia sterile water) was charged into a screw tube (manufactured by Maruemu Corporation, No. 5) in an amount shown in Table 2. The mixture was heated (at 90° C. to 105° C. for 60 minutes) in a dry bath incubator (manufactured by First Gene) to be dissolved and stirred until the solution was cooled to room temperature. The stirring was stopped, and the solution was left. A gel was formed in Example 2 and Example 3, but the solutions of Comparative Examples 1 to Comparative Example 3 without N-palmitoyl-Gly-His remained in a solution state.

Next, each of the gels and the solutions was poured using a spatula or a dropper into a 20 mm×20 mm square hole in a silicone sheet (manufactured by Tigers Polymer Corporation) having a thickness of 3 mm mounted on a glass substrate. The sheet base material was cooled at −24° C. for 30 minutes and then was left at room temperature (about 25° C.) for 30 minutes. The formation of a sheet was observed. The freezing (cooling at −24° C. for 30 minutes)-thawing (leaving at room temperature for 30 minutes) operation was repeated until a sheet was obtained, and the number of repetitions was counted as the number of repetitions of freezing-thawing. Table 2 shows the obtained results.

TABLE 2

Number of repetitions of freezing-thawing required until gel sheet formation (1)

| | Mixing amount (g) | | | | |
|---|---|---|---|---|---|
| Component | Example 2 | Example 3 | Comparative Example 1 | Comparative Example 2 | Comparative Example 3 |
| N-palmitoyl-Gly-His | 0.1 | 0.2 | 0 | 0 | 0 |
| PVA | 0.5 | 0.5 | 0.5 | 1.5 | 2 |
| Pure water | 9.4 | 9.3 | 9.5 | 8.5 | 8 |
| Number of repetitions of freezing-thawing | 2 | 1 | 5 | 2 | 1 |

As shown in Table 2, in Example 2 and Example 3 containing N-palmitoyl-Gly-His, the number of repetitions of freezing-thawing until each gel was solidified into a sheet form to form a gel sheet was one or two, revealing easy achievement of the sheet formation. In contrast, in Comparative Example 1 in which no N-palmitoyl-Gly-His was contained and PVA alone was contained at the same concentration as those in Example 2 and Example 3, the number of repetitions was five.

Increasing the concentration of PVA can reduce the number of repetitions of freezing-thawing (Comparative Example 2 and Comparative Example 3). However, the addition of N-palmitoyl-Gly-His can also reduce the number of repetitions of freezing-thawing even at a lower PVA concentration. This result shows that Example 2 and Example 3 have an advantage.

Example 4 to Example 6

Preparation of Gel Sheet by Freezing-Thawing Method (2)

Each of N-palmitoyl-Gly-His synthesized above, PVA (manufactured by Kuraray Co., Ltd.), and pure water (manufactured by Kyoei Pharmaceutical Industries, Ltd., Japanese Pharmacopoeia sterile water) was charged into a screw tube (manufactured by Maruemu Corporation, No. 5) in an amount shown in Table 3. Here, the amount was adjusted so that a single freezing-thawing process in a later step allowed a gel to be solidified into a sheet form. The mixture was heated (at 90° C. to 105° C. for 60 minutes) in a dry bath incubator (manufactured by First Gene) to be dissolved and stirred until the solution was cooled to room temperature. The stirring was stopped, and the solution was left. A gel was formed in Example 4 to Example 6.

Next, each of these gels was poured using a dropper into a 20 mm×20 mm square hole in a silicone sheet (manufactured by Tigers Polymer Corporation) having a thickness of 3 mm mounted on a glass substrate. The sheet base material was cooled at −24° C. for 30 minutes and then was left at room temperature (about 25° C.) for 30 minutes. The formation of a sheet was ascertained. Table 3 shows the obtained results.

TABLE 3

Number of repetitions of freezing-thawing required until gel sheet formation (2)

| | Mixing amount (g) | | | |
|---|---|---|---|---|
| Component | Example 4 | Example 5 | Example 6 | Comparative Example 3 (shown again) |
| N-palmitoyl-Gly-His | 0.05 | 0.1 | 0.2 | 0 |
| PVA | 1 | 1 | 0.5 | 2 |
| Pure water | 8.95 | 8.9 | 9.3 | 8 |
| Number of repetitions of freezing-thawing | 1 | 1 | 1 | 1 |
| Pure water content (w/w) | 89.5% | 89% | 93% | 80% |

As shown in Table 3, adding N-palmitoyl-Gly-His contained in a larger amount could reduce the amount of PVA required for the formation of a gel sheet. In particular, in Example 6, the addition of 0.2 g of N-palmitoyl-Gly-His allows PVA to be added in an amount of 0.5 g, thereby increasing the pure water content to 93% (w/w).

In contrast, in Comparative Example 3 (shown again) without N-palmitoyl-Gly-His, the solidification into a sheet form required 2 g of PVA, and thus the pure water content remained at 80% (w/w).

From the results shown in Table 3, in Example 4 to Example 6 with N-palmitoyl-Gly-His, water could be retained in a larger amount and the amount of PVA could be reduced. Hence, the gel sheet is expected to have advantageous effects of reducing stress such as a sticky feel and a squeak feel due to the increase in the amount of PVA and of improving a feel in use and a cold feel (cool feel) when the gel sheet is in contact with skin, for example.

Example 7, Example 8, and Comparative Example 4

Sensory Test of Gel Sheet

Each of N-palmitoyl-Gly-His synthesized above, PVA (manufactured by Kuraray Co., Ltd.), and pure water (manufactured by Kyoei Pharmaceutical Industries, Ltd., Japanese Pharmacopoeia sterile water) was charged into a screw tube (manufactured by Maruemu Corporation, No. 5) in an amount shown in Table 4. The mixture was heated (at 90° C. to 105° C. for 60 minutes) in a dry bath incubator (manufactured by First Gene) to be dissolved and stirred until the solution was cooled to room temperature. The stirring was stopped, and the solution was left. A gel was formed in Example 7 and Example 8, but the solution of Comparative Example 4 remained in a solution state.

Next, each of the gels and the solution was poured using a spatula or a dropper into a 20 mm×20 mm square hole in a silicone sheet (manufactured by Tigers Polymer Corporation) having a thickness of 3 mm mounted on a glass substrate. The sheet base material was cooled at −24° C. for 30 minutes and then was left at room temperature (about 25° C.) for 30 minutes. The freezing (cooling at −24° C. fix 30 minutes)-thawing (standing at room temperature for 30 minutes) operation was repeated twice, thereby affording a sheet.

The obtained gel sheet was disposed on and deposited to a polypropylene nonwoven fabric. Next, the gel sheet on the nonwoven fabric was applied onto the back of a hand, and then the nonwoven fabric was removed. Then, the sensory test of the gel sheet was carried out in a blind condition. Immediately after the sensory test, the hand was carefully washed with soap. In the sensory test, five items were evaluated in accordance with the criteria below.

<1. Criteria for Easy Application>

When a gel sheet on a nonwoven fabric was applied onto skin, a gel sheet that could be smoothly applied onto skin was evaluated as ○, and a gel sheet that was difficult to be applied was evaluated as x.

<2. Criteria for Texture>

When a gel sheet on a nonwoven fabric was applied onto skin, a gel sheet that could be applied onto a skin surface without a rough feel but with a smooth feel was evaluated as ○, a gel sheet that caused a little rough feel but was usable was evaluated as ρ, and a gel sheet that caused a smooth feel or a rough feel was evaluated as x.

<3. Criteria for Cold Feel>

When a gel sheet on a nonwoven fabric was applied onto skin, a gel sheet providing a cold feel (cool feel) concurrently with the application was evaluated as ○, and a gel sheet providing no cold feel was evaluated as x.

<4. Criteria for Stickiness>

When a gel sheet on a nonwoven fabric was applied onto skin and then the gel sheet was removed from the skin, a gel sheet that left no stickiness on the skin surface was evaluated as ○, a gel sheet that left a little stickiness but was usable was evaluated as Δ, and a gel sheet that left stickiness was evaluated as x.

<5. Criteria for Easy Removal>

When a gel sheet on a nonwoven fabric was applied onto skin, then dried, and removed from the skin, a gel sheet that was easily removed without wrinkles was evaluated as ○, a gel sheet that left a little residue but was usable was evaluated as Δ, and a gel sheet that partially adhered onto the skin to cause wrinkles and was difficult to be removed was evaluated as x.

Table 4 shows the obtained results.

TABLE 4

Gel sheet Sensory test result

| | | Mixing amount (g) | | |
| --- | --- | --- | --- | --- |
| Component | | Example 7 | Example 8 | Comparative Example 4 |
| N-palmitoyl-Gly-His | | 0.1 | 0.2 | 0 |
| PVA | | 0.5 | 0.5 | 0.5 |
| Pure water | | 9.4 | 9.3 | 9.5 |
| Sensory test result | 1. Easy application | ○ | ○ | x |
| | 2. Texture | Δ | ○ | x |
| | 3. Cold feel | ○ | ○ | ○ |
| | 4. Stickiness | Δ | ○ | x |
| | 5. Easy removal | Δ | Δ | x |

As shown in Table 4, Example 8 in which 0.2 g of N-palmitoyl-Gly-His and 0.5 g of PVA were contained showed good results in each of easy application, texture, cold feel, and stickiness. Example 7 in which N-palmitoyl-Gly-His was contained in an amount of 0.1 g showed good results in both easy application and cold feel but had small problems in the texture and the stickiness (Example 7). Each Example had a small problem in easy removal.

In contrast, Comparative Example 4 in which no palmitoyl-Gly-His was contained and 0.5 g of PVA alone was contained showed a good result in cold feel but basically had poor adhesiveness to the nonwoven fabric itself. The sheet was difficult to be applied (adhered) onto the skin and collapsed when applied onto skin. The sheet had poor texture and caused wrinkles when the sheet was removed. In addition, a large amount of the gel in the gel sheet remained on the skin. The sheet accordingly had problems in a feel in use.

After the sensory test, no skin trouble occurred, such as skin irritation and itchiness.

Example 9 to Example 13 and Comparative Example 5 to Comparative Example 8

Drug Formulation Test in Gel Sheet

In accordance with the procedure below, (−)-menthol, DL-camphor, (−)-menthol and DL-camphor, or urea was mixed as a drug with N-palmitoyl-Gly-His, PVA, and pure water, and the formation of a gel sheet was evaluated.

<Test Procedure>

Each of palmitoyl-Gly-His, PVA (manufactured by Kuraray Co., Ltd.), pure water (manufactured by Kyoei Pharmaceutical Industries, Ltd., Japanese Pharmacopoeia sterile water), and a drug was charged into a screw tube (manufactured by Maruemu Corporation, No. 2) in an amount shown in Table 5. The mixture was heated (at 90° C. to 105° C. for 60 minutes) in a dry bath incubator (manufactured by First Gene) to be dissolved and stirred until the solution was cooled to room temperature. The stirring was stopped, and the solution was left to yield a gel or a solution.

Next, each of the gels and the solutions was poured using a spatula or a dropper into a 20 mm×20 mm square hole in a silicone sheet (manufactured by Tigers Polymer Corporation) having a thickness of 3 mm mounted on a glass substrate. The sheet base material was cooled at −24° C. for 30 minutes and then was left at room temperature (about 25° C.) for 30 minutes. A sample forming a sheet was evaluated as ○, and a sample forming no sheet was evaluated as x.

Table 5 shows the obtained results.

1) Example 9 and Comparative Example 5

(−)-Menthol Formulation (−)-Menthol (manufactured by Tokyo Chemical Industry Co., Ltd.) was selected as a formulation drug (see Table 5). The mixture was heated in a dry bath incubator to be dissolved and was stirred until the solution was cooled to room temperature. After leaving the solution at room temperature, a gel was formed in Example 9, but the solution remained in Comparative Example 5 without N-palmitoyl-Gly-His.

2) Example 10 and Comparative Example 6

DL-Camphor Formulation

DL-Camphor (manufactured by Junsei Chemical Co., Ltd.) was selected as a formulation drug (see Table 5). The mixture was heated in a dry bath incubator to be dissolved and was stirred until the solution was cooled to room temperature. After leaving the solution at room temperature, a gel was formed in Example 10, but the solution remained in Comparative Example 6 without N-palmitoyl-Gly-His.

3) Example 11 and Comparative Example 7

(−)-Menthol and DL-Camphor Formulation (−)-Menthol (manufactured by Tokyo Chemical industry Co., Ltd.) and DL-camphor (manufactured by Junsei Chemical Co., Ltd.) were selected as formulation drugs (see Table 5). The mixture was heated in a dry bath incubator to be dissolved and was stirred until the solution was cooled to room temperature. After leaving the solution at room temperature, a gel was formed in Example 11, but the solution remained in Comparative Example 7 without N-palmitoyl-Gly-His.

4) Example 12, Example 13, and Comparative Example 8

Urea Formulation

Urea (manufactured by Junsei Chemical Co., Ltd.) was selected as a formulation drug (see Table 5). The mixture was heated in a dry bath incubator to be dissolved and was stirred until the solution was cooled to room temperature. After leaving the solution at room temperature, a gel was formed in Example 12 and Example 13, but the solution remained in Comparative Example 8 without N-palmitoyl-Gly-His.

(manufactured by Wako Pure Chemical Industries, Ltd., pH=7.4) was charged into a screw tube (manufactured by Maruemu Corporation, No. 5) in an amount shown in Table 6. The mixture was heated (at 100° C. for 60 minutes) in a dry bath incubator (manufactured by First Gene) and was left at room temperature for 16 hours. The gelation was ascertained by test tube inversion method. At the time, a sample without flowability was considered to be a gel.

Figure 6:
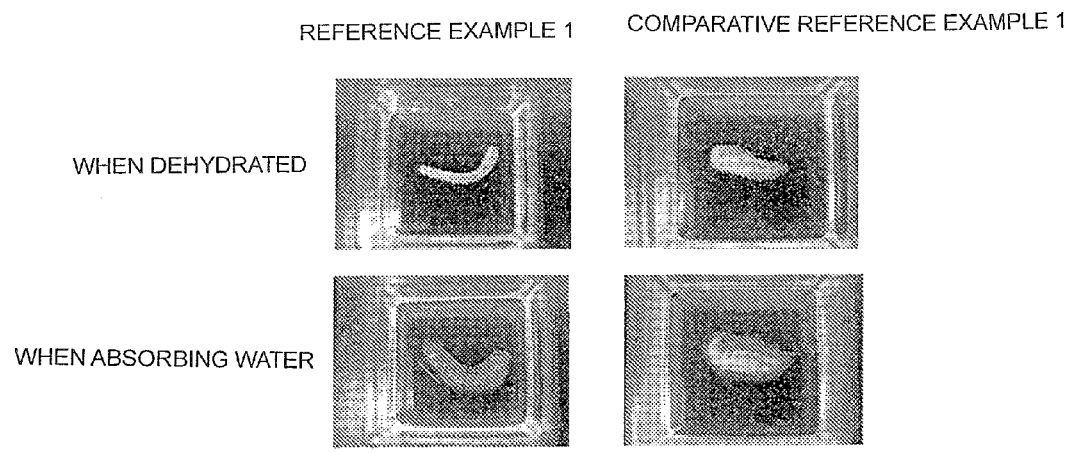
FIG. 6 is photographs showing gels that were obtained in Reference Examples and were formed into a fibrous shape and that were dehydrated or absorbed water.

The gel was transferred into a syringe (manufactured by Terumo Corporation) and was extruded into methanol (manufactured by Kanto Chemical Co., Inc.) cooled to −20° C. to be solidified into a fibrous form, thereby affording gel fibers. Next, methanol was removed and the residue was dried to yield dehydrated gel fibers (gel fibers when dehydrated). The obtained gel fibers were immersed in 3 mL of pure water in a non-electrostatic square styrol case (36 mm×36 mm×14 mm) to yield water-absorbed gel fibers (gel fibers when absorbing water). The change in the gel fiber shape between when dehydrated and when absorbing water was observed. FIG. 6 shows photographs of observations of the gel fibers when dehydrated and when absorbing water.

TABLE 6

Gel formulation used for gel spinning

| | Mixing amount (g) | |
|---|---|---|
| Component | Reference Example 1 | Comparative Reference Example 1 |
| N-palmitoyl-Gly-His | 0.1 | 0 |
| PVA | 1 | 1 |
| 50 mM phosphate buffer solution | 8.9 | 8.9 |

TABLE 5

Gel sheet Drug formulation test result

| | Mixing amount (g) | | | | | | | | |
|---|---|---|---|---|---|---|---|---|---|
| Component | Example 9 | Comparative Example 5 | Example 10 | Comparative Example 6 | Example 11 | Comparative Example 7 | Example 12 | Example 13 | Comparative Example 8 |
| N-palmitoyl-Gly-His | 0.1 | 0 | 0.1 | 0 | 1.0 | 0 | 0.1 | 0.1 | 0 |
| PVA | 1 | 1 | 1 | 1 | 1 | 1 | 1 | 1 | 1 |
| Pure water | 8.6 | 8.7 | 8.6 | 8.7 | 8.3 | 8.4 | 8.6 | 6.9 | 8.7 |
| (−)-menthol | 0.3 | 0.3 | — | — | 0.3 | 0.3 | — | — | — |
| DL-camphor | — | — | 0.3 | 0.3 | 0.3 | 0.3 | — | — | — |
| Urea | — | — | — | — | — | — | 0.3 | 2 | 0.3 |
| Sheet formability | o | x | o | x | o | x | o | o | x |

As shown in Table 5, in each drug formulation, no sheet was formed in Comparative Example 5 to Comparative Example 8 without N-palmitoyl-Gly-His.

In contrast, in each of Example 9 to Example 13 in which 0.1 g (1% (w/w)) of N-palmitoyl-Gly-His was contained, the formation of a gel sheet was ascertained. In particular, as shown in Example 13, when urea was contained at a high concentration of 20% (w/w), the sheet formation was ascertained.

Reference Example

Preparation of Gel Fiber

Each of N-palmitoyl-Gly-His synthesized above, PVA (manufactured by Wako Pure Chemical Industries, Ltd., n=1,500 to 1,800), and 50 mM phosphate buffer solution In Reference Example 1 containing N-palmitoyl-Gly-His, when a gel was extruded from a syringe into methanol followed by dehydration, gel fibers maintaining a fibrous shape were obtained. In addition, the gel fiber maintained its shape even when absorbing water. In other words, it was ascertained that the gel used in the gel sheet of the present invention can be stored in a drying condition while maintaining various shapes, for example, the sheet shape described above or the fibrous shape.

In contrast, in Comparative Reference Example 1 without N-palmitoyl-Gly-His, a gel extruded from a syringe into methanol followed by dehydration could not maintain a certain shape such as a fibrous shape. In addition, when the gel adsorbs water, dissolution of PVA started. Thus, the gel could not maintain its shape and was fragile.

In other words, it was revealed that forming a gel from a mixture of N-palmitoyl-Gly-His and PVA as a gelator improved the formability of a gel shape and greatly increased the strength of spun fibers.

The gel fiber obtained in such a manner is also expected to be used for various applications, especially to be applied to wound dressings, as with the gel sheet of the present invention, and for example, can be used in combination with the laminate (what is called an adhesive patch) prepared by using the gel sheet of the present invention.

Example 14

Sheet Formation of Palmitoyl-Gly-His Hydrogel Using Ethanol Immersion Liquid (Ethanol-Immersed Sheet)

Into a screw tube (manufactured by Maruemu Corporation, No. 5), 0.1 g N-palmitoyl-Gly-His synthesized above, 1 g of PVA (manufactured by Wako Pure Chemical Industries, Ltd., average degree of polymerization n=1,500 to 1,800), and 8.9 g of 50 mM phosphate buffer solution (manufactured by Wako Pure Chemical Industries, Ltd., pH=7.4) were charged. The mixture was heated (at 95° C. for 60 minutes) in an aluminum block bath (manufactured by Taitec Ltd.) to be dissolved. Into a petri dish (diameter 85 mm×height 15 mm), 10 mL of the solution was transferred and was allowed to stand and cool. After 16 hours, the gelation was ascertained by inversion method. At the time, a sample without flowability was considered to be a gel.

Next, to the gel, 10 mL of 99.5% ethanol was dropped, and operation of exchanging the ethanol was conducted twice every 1 hour. The gel was immersed in ethanol for 16 hours including the period of time for the operation to afford a white, ethanol-immersed sheet.

Example 15

Production of Water Retention Sheet of Palmitoyl-Gly-His Hydrogel Using Ethanol Immersion Liquid (Water-Substituted Sheet After Ethanol Immersion)

Into a screw tube (manufactured by Maruemu Corporation, No. 5), 0.1 g of N-palmitoyl-Gly-His synthesized above, 1 g of PVA (manufactured by Wako Pure Chemical Industries, Ltd., average degree of polymerization n=1,500 to 1,800), and 8.9 g of 50 mM phosphate buffer solution (manufactured by Wako Pure Chemical Industries, Ltd., pH=7.4) were charged. The mixture was heated (at 95° C. for 60 minutes) in an aluminum block bath (manufactured by Taitec Co., Ltd.) to be dissolved. Into a petri dish (diameter 85 mm×height 15 mm), 10 mL of the solution was transferred and was allowed to stand and cool. After 16 hours, the gelation was ascertained by inversion method. At the time, a sample without flowability was considered to be a gel.

Next, to the gel, 10 mL of 99.5% ethanol was dropped, and operation of exchanging the ethanol was conducted twice every 1 hour. The gel was immersed in ethanol for 16 hours including the period of time for the operation to afford a sheet. Then, to the sheet, 10 mL of pure water was dropped, and operation of exchanging the pure water was conducted twice every 1 hour. The gel was immersed in pure water for 16 hours including the period of time for the operation to afford a white, water-substituted sheet after ethanol immersion.

Example 16

Sheet Formation of Palmitoyl-Gly-His Hydrogel Using 50% Aqueous Ethanol Immersion Liquid Into a screw tube (manufactured by Maruemu Corporation, No. 5), 0.1 g of N-palmitoyl-Gly-His synthesized above, 1 g of PVA (manufactured by Wako Pure Chemical Industries, Ltd., average degree of polymerization n=1,500 to 1,800), and 8.9 g of 50 mM phosphate buffer solution (manufactured by Wako Pure Chemical Industries, Ltd., pH=7.4) were charged. The mixture was heated (at 95° C. for 60 minutes) in an aluminum block bath (manufactured by Taitec Co., Ltd.) to be dissolved. Into a petri dish (diameter 85 mm×height 15 mm), 10 mL of the solution was transferred) and was allowed to stand and cool. After 16 hours, the gelation was ascertained by inversion method. At the time, a sample without flowability was considered to be a gel.

Next, to the gel, 10 mL of 50% aqueous ethanol was dropped, and a transparent sheet was obtained after 1 hour.

Example 17

Sheet Formation of Palmitoyl-Gly-His Hydrogel Using 70% Aqueous Ethanol Immersion Liquid Into a screw tube (manufactured by Maruemu Corporation, No. 5), 0.1 g of N-palmitoyl-Gly-His synthesized above, 1 g of gelatin (manufactured by Wako Pure Chemical Industries, Ltd., derived from bovine bone), and 8.9 g of 50 mM phosphate buffer solution (manufactured by Wako Pure Chemical Industries, Ltd., pH=7.4) were charged. The mixture was heated (at 95° C. for 60 minutes) in an aluminum block bath (manufactured by Taitec Co., Ltd.) to be dissolved. Into a petri dish (diameter 85 mm×height 15 mm), 10 mL of the solution was transferred and was allowed to stand and cool. After 16 hours, the gelation was ascertained by inversion method. At the time, a sample without flowability was considered to be a gel.

Next, to the gel, 10 ml, of 70% aqueous ethanol was dropped, and a stretch white sheet was obtained after 5 hours.

Example 18

Sheet Formation of Palmitoyl-Gly-His Hydrogel Using Methanol Immersion Liquid (Methanol-Immersed Sheet)

Into a screw tube (manufactured by Maruemu Corporation, No. 5), 0.1 g of N-palmitoyl-Gly-His synthesized above, 1 g of PVA (manufactured by Wake Pure Chemical Industries, Ltd., average degree of polymerization n=1,500 to 1,800), and 8.9 g of 50 mM phosphate buffer solution (manufactured by Wako Pure Chemical Industries, Ltd., pH=7.4) were charged. The mixture was heated (at 95° C. for 60 minutes) in a dry bath incubator aluminum block bath (manufactured by Taitec Co., Ltd.) to be dissolved. Into a petri dish (diameter 85 mm×height 15 mm), 10 mL of the solution was transferred and was allowed to stand and cool. After 16 hours, the gelation was ascertained by inversion method. At the time, a sample without flowability was considered to be a gel.

Next, to the gel, 10 mL of 99.5% methanol was dropped, and the gel was immersed in methanol for 16 hours to afford a white, methanol-immersed sheet.

Example 19

Production of Water Retention Sheet of Palmitoyl-Gly-His Hydrogel Using Methanol Immersion Liquid (Water-Substituted Sheet after Methanol Immersion)

Into a screw tube (manufactured by Maruemu Corporation, No. 5), 0.1 g of N-palmitoyl-Gly-His synthesized above, 1 g of PVA (manufactured by Wako Pure Chemical Industries, Ltd., average degree of polymerization n=1,500 to 1,800), and 8.9 g of 50 mM phosphate buffer solution (manufactured by Wako Pure Chemical Industries, Ltd., pH===7.4) were charged. The mixture was heated (at 95° C. for 60 minutes) in a dry bath incubator (manufactured by First Gene) to be dissolved. Into a petri dish (diameter 85 mm×height 15 mm), 10 ml, of the solution was transferred and was allowed to stand and cool. After 16 hours, the gelation was ascertained by inversion method. At the time, a sample without flowability was considered to be a gel.

Next, to the gel, 10 mL of 99.5% methanol was dropped, and the gel was immersed in methanol for 16 hours to afford a methanol-immersed sheet. Then, to the sheet, 10 mL of pure water was dropped, and operation of exchanging the pure water was conducted twice every 1 hour. The gel was immersed in pure water for 16 hours including the period of time for the operation to afford a white, water-substituted sheet after methanol immersion.

<Static Viscoelasticity>

Breaking stress and breaking deformation distance of each sheet obtained in Example 14, Example 15, Example 18, and Example 19 were measured as the parameters of static viscoelasticity with a creep meter (RE-33005B, manufactured by Yamaden Co., Ltd.). In other words, each sheet was placed on a measurement plate, and the breaking stress and the breaking deformation distance of each of the ethanol-immersed sheet (Example 14), the water-substituted sheet after ethanol immersion (Example 15), the methanol-immersed sheet (Example 18), and the water-substituted sheet after methanol immersion (Example 19) were measured using a spherical plunger under the condition of load cell: 200 N, amplifier magnification: ×10, storing pitch: 0.03 second, measurement distortion factor: 99.95%, measurement speed: 1 mm/second, sample thickness: 20 mm, contact area diameter: 1.5 mm, and room temperature.

Figure 10:
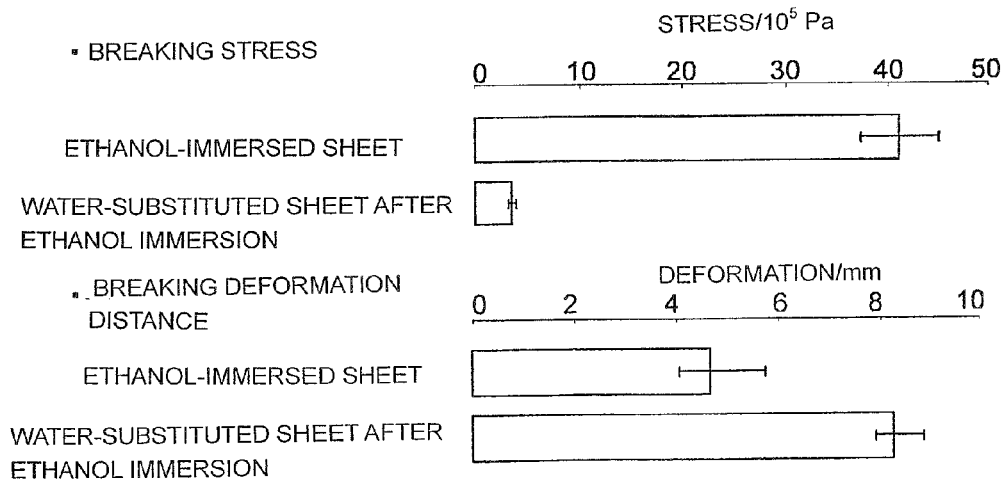
FIG. 10 is a graph showing breaking stresses and breaking deformation distances of an ethanol-immersed sheet obtained in Example 14 and a water-substituted sheet after the ethanol immersion obtained in Example 15.
Figure 11:
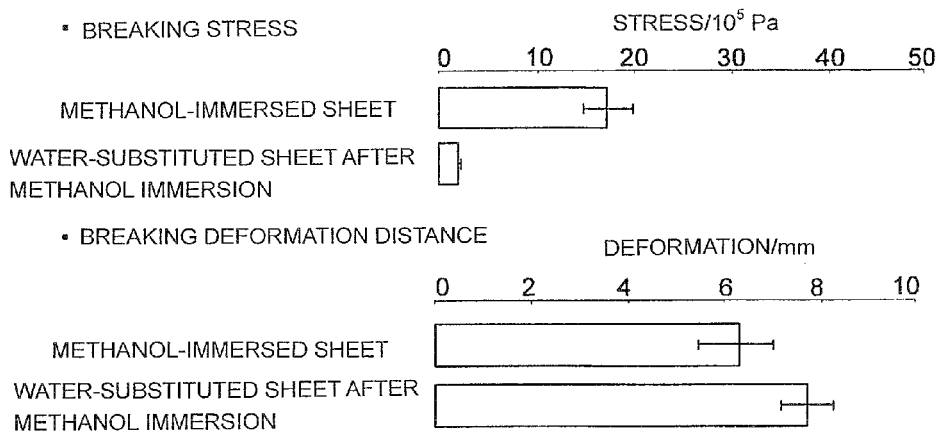
FIG. 11 is a graph showing breaking stresses and breaking deformation distances of a methanol-immersed sheet obtained in Example 18 and a water-substituted sheet after the methanol immersion obtained in Example 19.

FIG. 10 and FIG. 11 show the obtained results.

As shown in FIG. 10, comparing the ethanol-immersed sheet and the water-substituted sheet after ethanol immersion, the ethanol-immersed sheet had a higher breaking stress and the water-substituted sheet after ethanol immersion had a longer breaking deformation distance. In other words, it was revealed that the sheet after the ethanol immersion (after solidification) is a hard nonstretch sheet but when supplied with water by water substitution, the sheet becomes a soft stretch sheet having water retention characteristics.

As shown in FIG. 11, comparing the methanol-immersed sheet and the water-substituted sheet after methanol immersion, the methanol-immersed sheet had a higher breaking stress and the water-substituted sheet after methanol immersion had a longer breaking deformation distance. In other words, it was revealed that the sheet after the methanol immersion (after solidification) is a hard nonstretch sheet but when supplied with water by water substitution, the sheet becomes a soft stretch sheet having water retention characteristics.

From these results, it is supposed that the nanofibrous structure of N-palmitoyl-Gly-His and the polyvinyl alcohol structure in the gel sheet solidified by immersion in ethanol or methanol can flow while physically bonding to each other in a balanced manner due to water substitution.

<Observation of Methanol-Immersed Sheet Containing N-Palmitoyl-Gly-His Under Scanning Electron Microscope (SEM)>

Figure 12:
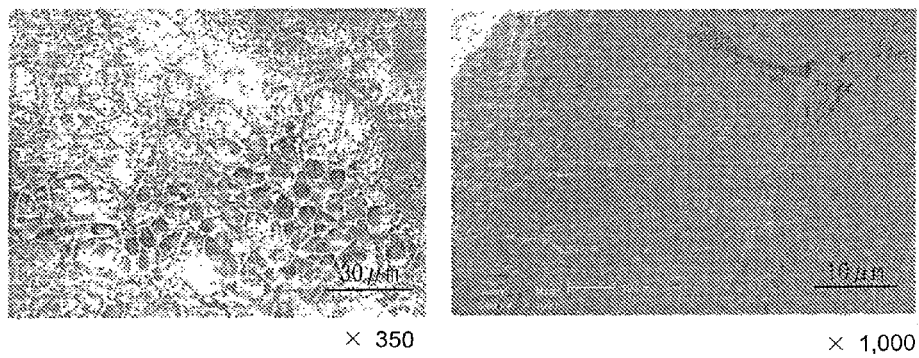
FIG. 12 shows photographs of the methanol-immersed sheet obtained in Example 18 observed under a scanning electron microscope with an energy dispersive X-ray analyzer (FIG. 12A: ×350.

The methanol-immersed sheet obtained in Example 18 was subjected to low vacuum observation under a scanning electron microscope (SEM) with an energy dispersive X-ray analyzer (manufactured by Shimadzu Corporation). FIG. 12 shows the obtained results.

As shown in FIG. 12, in the solidified gel, the fibers of N-palmitoyl-Gly-His were also observed (FIG. 12A), and a large number of stoma-like pores were observed on the sheet surface (FIG. 12B)).

In other words, the results reveal that the pores can cause the gel sheet containing N-palmitoyl-Gly-His to provide water absorption mechanism and can control the deformation and the strength of the gel sheet.

Example 20

Transparent Water-Substituted Sheet After 50% Aqueous Ethanol Immersion

Into a screw tube (manufactured by Maruemu Corporation, No. 5), 0.1 g of N-palmitoyl-Gly-His synthesized above, 1 g of PVA (manufactured by Wako Pure Chemical Industries, Ltd., average degree of polymerization n=1,500 to 1,800), and 8.9 g of 50 mM phosphate buffer solution (manufactured by Wako Pure Chemical Industries, Ltd., pH=7.4) were charged. The mixture was heated (at 95° C. for 60 minutes) in a dry bath incubator (manufactured by First Gene) to be dissolved. Into a petri dish (diameter 85 mm×height 15 mm), 10 mL of the solution was transferred and was allowed to stand and cool. After 16 hours, the gelation was ascertained by inversion method. At the time, a sample without flowability was considered to be a gel.

Next, to the gel, 10 mL of 50% aqueous ethanol was dropped, and operation of exchanging the 50% aqueous ethanol was conducted twice every 1 hour. The gel was immersed in 50% aqueous ethanol for 16 hours including the period of time for the operation to afford a 50% aqueous ethanol-immersed transparent sheet.

Reference Example

Preparation of Each Solution Used for Formation of Hydrogel Sheet Using Sodium Lactate Immersion Liquid (a-1) Preparation of 5% PVA-Phosphate Buffer Solution Into a heat-resistant glass screw bottle (manufactured by iwaki (AGC Techno Glass Co., Ltd.), 100 mL), 47.5 g of phosphate buffer solution (phosphate buffer powder manufactured by Wako Pure Chemical Industries, Ltd., 1/15 mol/L, pH 7.4, composition: 7.6 g of $Na_2HPO_4$ and 1.8 g of $KH_2PO_4$ in 1 L of pure water) and 2.5 g of PVA (JF17, Japan Vam & Poval Co., Ltd.) were charged. The mixture was heated in a dry bath incubator (manufactured by First Gene) at 90° C. for 60 minutes. After visual confirmation of the dissolution, the solution was cooled at room temperature to afford an aqueous solution.

(a-2) Preparation of 6.4% PVA-Phosphate Buffer Solution

Into a heat-resistant glass screw bottle (manufactured by iwaki (AGC Techno Glass Co., Ltd.), 100 mL), 58.5 g of phosphate buffer solution (phosphate buffer powder manufactured by Wako Pure Chemical Industries, Ltd., 1/15 mol/L, pH 7.4, composition: 7.6 g of $Na_2HPO_4$ and 1.8 g of $KH_2PO_4$ in 1 L of pure water) and 4 g of PVA (JF17, Japan Vam & Poval Co., Ltd.) were charged. The mixture was heated in a dry bath incubator (manufactured by First Gene) at 90° C. for 90 minutes. After visual confirmation of the dissolution, the solution was cooled at room temperature to afford an aqueous solution.

(a-3) Preparation of 8.8% PVA-Phosphate Buffer Solution

Into a heat-resistant glass screw bottle (manufactured by iwaki (AGC Techno Glass Co., Ltd.), 200 mL), 145 g of phosphate buffer solution (phosphate buffer powder manufactured by Wako Pure Chemical Industries, Ltd., 1/15 mol/L, pH=7.4, composition: 7.6 g of $Na_2HPO_4$ and 1.8 g of $KH_2PO_4$ in 1 L of pure water) and 14 g of PVA (JF17, Japan Vam & Poval Co., Ltd.) were charged. The mixture was heated in a dry bath incubator (manufactured by First Gene) at 90° C. for 90 minutes. After visual confirmation of the dissolution, the solution was cooled at room temperature to afford an aqueous solution.

(b-1) Preparation of 20% Palmitoyl-Gly-His Free Form Dispersion Liquid in Pentylene Glycol Into a glass vial tube with a cap (manufactured by Maruemu Corporation, No. 7), 4 g of free form of palmitoyl-Gly-His synthesized in Synthesis Example 1 and 16 g of pentylene glycol (manufactured by Junsei Chemical Co., Ltd.) were charged. The mixture was heated (at 90° C. for 30 minutes) in a dry bath incubator (manufactured by First Gene) and then was cooled at room temperature to afford a dispersion liquid.

(b-2) Preparation of 5.13% Palmitoyl-Gly-His Free Form Dispersion Liquid in 1,2-Hexanediol Into a glass vial tube with a cap (manufactured by Maruemu Corporation, No. 7), 0.5 g of free form of palmitoyl-Gly-His synthesized in Synthesis Example 1, 1 g of 1,2-hexanediol (manufactured by ITO), and 8.25 g of pure water were charged. The mixture was heated (at 80° C. for 30 minutes) in a dry bath incubator (manufactured by First Gene) to afford a dispersion liquid.

(c) Preparation of 2% Aqueous Sodium Alginate Solution

Into a glass vial tube with a cap (manufactured by Maruemu Corporation, No. 7), 0.5 g of sodium alginate (manufactured by Kikkoman Biochemifa Company) and pure water were charged to make a volume of 50 mL, and the mixture was shaken to afford an aqueous solution.

(d) Preparation of 2.5% Aqueous Sodium Polyacrylate Solution

Into a heat-resistant glass screw bottle (manufactured by iwaki (AGC Techno Glass Co., Ltd.), 100 mL), 97.5 g of pure water and 2.5 g of sodium polyacrylate (manufactured by ITO) were charged. The mixture was heated in a dry bath incubator (manufactured by First Gene) at 80° C. for 60 minutes. After visual confirmation of the dissolution, the solution was cooled at room temperature to afford an aqueous solution.

(e) Preparation of 2% Aqueous Laponite XLG Solution

Into a heat-resistant glass screw bottle (manufactured by iwaki (AGC Techno Glass Co., Ltd.), 100 mL), 48.75 g of pure water and 1.25 g of Laponite XLG (manufactured by RockWood Additives) were charged. The mixture was heated in a dry bath incubator (manufactured by First Gene) at 80° C. for 60 minutes. After visual confirmation of the dissolution, the solution was cooled at room temperature to afford an aqueous solution.

(f) 40% Aqueous Sodium Lactate Solution

To 40 g of 50% aqueous sodium lactate solution (manufactured by Junsei Chemical Co., Ltd.), 10 g of pure water was added to afford a 40% aqueous sodium lactate solution.

(g) Preparation of 4% Aqueous PVA Solution

Into a 150-mL glass bottle (manufactured by Hakuyo Glass Co., Ltd.), 2 g of PVA (JF17, Japan Vam & Poval Co., Ltd.) and 48 g of pure water were charged. The mixture was heated in a dry bath incubator (manufactured by First Gene) at 100° C. for 60 minutes. After visual confirmation of the dissolution, the solution was cooled at room temperature to afford an aqueous solution.

(h) Preparation of 1% Palmitoyl-Gly-His, 2% PVA Dispersion Liquid

Into a 150-mL glass bottle (manufactured by Hakuyo Glass Co., Ltd.), 1 g of palmitoyl-Gly-His synthesized in Synthesis Example 1, 1 g of phosphate buffer powder (manufactured by Wako Pure Chemical Industries, Ltd.), and 48 g of pure water were charged. The mixture was heated in a dry bath incubator (manufactured by First Gene) at 100° C. for 60 minutes to be dissolved. To the solution, 50 g of 4% aqueous PVA solution previously prepared in (g) was mixed. The mixture was heated at 95° C. for 30 minutes, and then was stirred using an ultra-magnetic stirrer (manufactured by Nissin Rika Co, Ltd., SW-RS077) at room temperature for 30 minutes at 300 rpm to afford a white dispersion liquid (gelled after standing).

Example 21

Sheet Formation of Palmitoyl-Gly-His Hydrogel Using Sodium Lactate Immersion Liquid (1)

Into a glass vial tube with a cap (manufactured by Maruemu Corporation, No. 7), 6.3 g of 8.8% PVA-phosphate buffer solution previously prepared in (a-3), 0.4 g of 20% palmitoyl-Gly-His free form dispersion liquid in pentylene glycol in (b-1), 1.5 g of 2% aqueous sodium alginate solution in (c), 0.4 g of glycerin (manufactured by ITO), and 0.4 g of 1,3-butylene glycol (manufactured by ITO) were charged. The mixture was heated in a dry bath incubator (manufactured by First Gene) at 80° C. for 30 minutes to be dissolved. About 4 g of the solution was poured into a glass petri dish (an inner diameter of 6.5 cm), and was left at room temperature for 20 minutes to make a gel. Next, 5 g of 40% aqueous sodium lactate solution in (f) was added into the petri dish, and the gel was immersed for 20 minutes. Then, the gel was washed with 10 g of pure water three times to afford a translucent sheet.

As the parameters for static viscoelasticity of the sheet, the breaking stress and the breaking deformation distance were measured with a creep meter (RE-33005B, manufactured by Yamaden Co Ltd.). In other words, the sheet was placed on a measurement plate, and the breaking stress and the breaking deformation distance of the sheet washed after the aqueous sodium lactate solution immersion were measured using a spherical plunger under the condition of load cell: 200 N, amplifier magnification: ×10, storing pitch: 0.03 second, measurement distortion factor: 99.95%, measurement speed: 1 mm/second, sample thickness: 20 mm, contact area diameter: 1.5 mm, and room temperature.

The breaking stress was $2.48 \times 10^5$ Pa and the breaking deformation distance was 4.98 mm.

Example 22

Sheet Formation of Palmitoyl-Gly-His Hydrogel Using Sodium Lactate Immersion Liquid (2)

Into a glass vial tube with a cap (manufactured by Maruemu Corporation, No. 7), 5.5 g of 5% PVA-phosphate buffer solution previously prepared in (a-1), 2 g of 5.13% palmitoyl-Gly-His free form dispersion liquid in hexanediol in (b-2), 1.5 g of 2% aqueous sodium alginate solution in (c), and 0.5 g of propylene glycol (manufactured by Junsei Chemical Co., Ltd.) were charged. The mixture was heated in a dry bath incubator (manufactured by First Gene) at 80° C. for 30 minutes to be dissolved. About 4 g of the solution was poured into a glass petri dish (an inner diameter of 6.5 cm), and was left at room temperature for 10 minutes to make a gel. Next, 5 g of 40% aqueous sodium lactate solution in (f) was added into the petri dish, and the gel was immersed for 10 minutes. Then, the gel was washed with 10 g of pure water three times to afford a translucent sheet.

As the parameters for static viscoelasticity of the sheet, the breaking stress and the breaking deformation distance were measured with a creep meter (RE-33005B, manufactured by Yamaden Co., Ltd.). In other words, the sheet was placed on a measurement plate, and the breaking stress and the breaking deformation distance of the sheet washed after the aqueous sodium lactate solution immersion were measured using a spherical plunger under the condition of load cell: 200 N, amplifier magnification: ×10, storing pitch: 0.03 second, measurement distortion factor: 99.95%, measurement speed: 1 mm/second, sample thickness: 20 mm, contact area diameter: 1.5 mm, and room temperature.

The breaking stress was $1.38 \times 10^5$ Pa and the breaking deformation distance was 2.51 mm.

Example 23

Sheet Formation of Palmitoyl-Gly-His Hydrogel Using Sodium Lactate Immersion Liquid (3)

Into a glass vial tube with a cap (manufactured by Maruemu Corporation, No. 7), 5 g of 1% palmitoyl-Gly-His, 2% PVA dispersion liquid previously prepared in (h) was charged. The dispersion liquid was heated in a dry bath incubator (manufactured by First Gene) at 80° C. for 5 minutes to be dissolved. About 4 g of the solution was poured into a stainless steel petri dish (an inner diameter of 5.5 cm), and was left at room temperature for 5 minutes to make a gel. Next, 5 g of 50% aqueous sodium lactate solution (manufactured by Junsei Chemical Co., Ltd.) was added into the petri dish, and the gel was immersed for 10 minutes. Then, the gel was washed with 10 g of pure water three times to afford a translucent sheet.

Example 24

Sheet Formation of Palmitoyl-Gly-His Hydrogel Using Sodium Lactate Immersion Liquid (4)

Into a glass vial tube with a cap (manufactured by Maruemu Corporation, No. 7), 4.28 g of 1% palmitoyl-Gly-His, 2% PVA dispersion liquid previously prepared in (ii), 0.02 g of polyvinylpyrrolidone (manufactured by BASF Japan Ltd.), and 0.7 g of propylene glycol (manufactured by Junsei Chemical Co., Ltd.) were charged. The mixture was heated in a dry bath incubator (manufactured by First Gene) at 80° C. for 5 minutes to be dissolved. About 4 g of the solution was poured into a stainless steel petri dish (an inner diameter of 5.5 cm), and was left at room temperature for 5 minutes to make a gel. Next, 5 g of 50% aqueous sodium lactate solution (manufactured by Junsei Chemical Co., Ltd.) was added into the petri dish, and the gel was immersed for 10 minutes. Then, the gel was washed with 10 g of pure water three times to afford a translucent sheet.

Example 25

Sheet Formation of Palmitoyl-Gly-His Hydrogel Using Sodium Lactate Immersion Liquid (5)

About 4 g of 1% palmitoyl-Gly-His, 2% PVA dispersion liquid previously prepared (h) was poured into a stainless steel petri dish (an inner diameter of 5.5 cm), and was left at room temperature for 5 minutes to make a gel. Next, 5 g of 50% aqueous sodium lactate solution (manufactured by Junsei Chemical Co., Ltd.) was added into the petri dish, and the gel was immersed for 10 minutes. Then, the gel was washed with 10 g of pure water three times to afford a white sheet.

Example 26

Sheet Formation of Palmitoyl-Gly-His Hydrogel Using Cellulose Support Medium

Into a glass vial tube with a cap (manufactured by Maruemu Corporation, No. 7), 5 g of 1% palmitoyl-Gly-His, 2% PVA dispersion liquid previously prepared in (h) was charged. The dispersion liquid was heated in a dry bath incubator (manufactured by First Gene) at 80° C. for 5 minutes to be dissolved. The solution was dropped on cellulose fiber (manufactured by Advantec Toyo Kaisha, Ltd., qualitative filter paper No. 101, 55 mm) placed on a stainless steel petri dish (an inner diameter of 5.5 cm), and was left at room temperature for 5 minutes to make a gel. Next, 5 g of 50% aqueous sodium lactate solution (manufactured by Junsei Chemical Co., Ltd.) was added into the petri dish, and the gel supported on the cellulose was immersed for 10 minutes. Then, the gel was washed with 10 g of pure water three times to afford a sheet with cellulose as a support medium.

Example 27

Sheet Containing Sodium Polyacrylate Using Sodium Lactate Immersion Liquid

Into a glass vial tube with a cap (manufactured by Maruemu Corporation, No. 7), 5.3 g of 6.4% PVA-phosphate buffer solution previously prepared in (a-2), 0.4 g of 20% palmitoyl-Gly-His free form dispersion liquid in pentylene glycol in (b-1), 1.5 g of 2% aqueous sodium alginate solution in (c), 0.4 g of glycerin (manufactured by ITO), 0.4 g of 1,3-butylene glycol (manufactured by ITO), and 1.5 g of 2.5% sodium polyacrylate in (d) were charged. The mixture was heated in a dry bath incubator (manufactured by First Gene) at 80° C. for 30 minutes to be dissolved. About 4 g of the solution was poured into a glass petri dish (an inner diameter of 6.5 cm), and was left at room temperature for 20 minutes to make a gel. Next, 5 g of 40% aqueous sodium lactate solution in (t) was added into the petri dish, and the gel was immersed for 20 minutes. Then, the gel was washed with 10 g of pure water three times to afford a translucent sheet.

As the parameters for static viscoelasticity of the sheet, the breaking stress and the breaking deformation distance were measured with a creep meter (RE-33005B, manufactured by Yamaden Co., Ltd.). In other words, the sheet was placed on a measurement plate, and the breaking stress and the breaking deformation distance of the sheet washed after the aqueous sodium lactate solution immersion were measured using a spherical plunger under the condition of load cell: 200 N, amplifier magnification: ×10, storing pitch: 0.03 second, measurement distortion factor: 99.95%, measurement speed: 1 mm/second, sample thickness: 20 mm, contact area diameter: 1.5 mm, and room temperature.

The breaking stress was $1.96 \times 10^5$ Pa and the breaking deformation distance was 3.81 mm.

Example 28

Sheet Containing Sodium Polyacrylate and Laponite XLG Using Sodium Lactate Immersion Liquid Into a glass vial tube with a cap (manufactured by Maruemu Corporation, No. 7), 5.8 g of 6.4% PVA-phosphate buffer solution previously prepared in (a-2), 0.4 g of 20% palmitoyl-Gly-His free form dispersion liquid in pentylene glycol in (b-1), 2 g of 2% aqueous sodium alginate solution in (c), 0.4 g of glycerin (manufactured by ITO), 0.4 g of 1,3-butylene glycol (manufactured by ITO), 1 g of 2.5% sodium polyacrylate in (d), and 0.5 g of 2% Laponite XLG in (e) were charged. The mixture was heated in a dry bath incubator (manufactured by First Gene) at 95° C. for 60 minutes to be dissolved. About 4 g of the solution was poured into a glass petri dish (an inner diameter of 6.5 cm), and was left at room temperature for 20 minutes to make a gel. Next, 5 g of 50% aqueous sodium lactate solution (manufactured by Junsei Chemical Co., Ltd.) was added into the petri dish, and the gel was immersed for 240 minutes. Then, the gel was washed with 10 g of pure water three times to afford a white sheet.

As shown in Example 21 to Example 28, using a lactic acid salt allowed a soft stretch sheet having water retention characteristics to be obtained without conducting immersion with an alcohol (for example, ethanol) and substitution with water.

Example 29, Example 30, Comparative Example 9, and Comparative Example 10

Preparation of Palmitoyl-Gly-His Gel Sheet Using Cross-Linking Agent and Sensory Evaluation Each of palmitoyl-Gly-His, PVA (manufactured by Japan Vam & Poval Co Ltd.), polyvinylpyrrolidone (manufactured by BASF Japan Ltd.), and 50 mM phosphate buffer solution (pH 7.5) was charged into a screw tube (manufactured by Maruemu Corporation, No. 5) in an amount shown in Table 7. The mixture was heated (at 90° C. to 105° C. for 60 minutes) in a dry bath incubator (manufactured by First Gene). The mixture was left at room temperature, and then was stirred at 500 rpm. A viscous sol was formed in Comparative Example 9 and Comparative Example 10, and a gel was formed in Example 29 and Example 30. Into each product, titanium diisopropoxybis(triethanolaminate) (manufactured by Matsumoto Fine Chemical Co., Ltd.) was added as a cross-linking agent while stirring the product with a vortex mixer. The mixture was poured into a styrol square case (type 2) (manufactured by As One Corporation), was left at room temperature for 1 day, and the sheet formation was wholly observed.

Each gel sheet obtained was applied onto the back of a hand, and then sensory test of the gel sheet was carried out in a blind condition. Immediately after the sensory test, the hand was carefully washed with soap. The sensory test result was evaluated on five items in accordance with the criteria below.

<1. Criteria for Easy Application>

When a gel sheet was applied onto skin, a gel sheet that could be smoothly applied onto skin was evaluated as ○, and a gel sheet that was difficult to be applied was evaluated as x.

<2. Criteria for Texture>

When a gel sheet was applied onto skin, a gel sheet that could be applied onto a skin surface without a rough feel but with a smooth feel was evaluated as ○, a gel sheet that caused a little rough feel but was usable was evaluated as ρ, and a gel sheet that caused a smooth feel or a rough feel was evaluated as x.

<3. Criteria for Cold Feel>

When a gel sheet was applied onto skin, a gel sheet providing a cold feel (cool feel) concurrently with the application was evaluated as ○, and a gel sheet providing no cold feel was evaluated as x.

<4. Criteria for Stickiness>

When a gel sheet was applied onto skin and then the gel sheet was removed from the skin, a gel sheet that left no stickiness on the skin surface was evaluated as ○, a gel sheet that left a little stickiness but was usable was evaluated as Δ, and a gel sheet that left stickiness was evaluated as x.

<5. Criteria for Easy Removal>

When a gel sheet was applied onto skin, then dried, and removed from the skin, a gel sheet that was easily removed without wrinkles was evaluated as ○, a gel sheet that left a little residue but was usable was evaluated as Δ, and a gel sheet that partially adhered onto the skin to cause wrinkles and was difficult to be removed was evaluated as x.

Table 7 shows the obtained results.

TABLE 7

Sensory test result of palmitoyl-Gly-His gel sheet using cross-linking agent

| Component | Example 29 | Example 30 | Comparative Example 9 | Comparative Example 10 |
|---|---|---|---|---|
| Free Form of N-palmitoyl-Gly-His | 0.025 g | 0.025 g | 0 g | 0 g |
| PVA | 0.5 g | 0.5 g | 0.5 g | 0.5 g |
| Polyvinylpyrrolidone | 0.2 g | 0 g | 0.2 g | 0 g |

TABLE 7-continued

Sensory test result of palmitoyl-Gly-His gel sheet using cross-linking agent

| Component | | Example 29 | Example 30 | Comparative Example 9 | Comparative Example 10 |
|---|---|---|---|---|---|
| Titanium diisopropoxybis(triethanolaminate) | | 0.4 g | 0.4 g | 0.4 g | 0.4 g |
| 50 mM phosphate buffer solution | | 8.875 g | 9.075 g | 8.9 g | 9.1 g |
| Sensory test result | 1. Easy application | ◯ | ◯ | ◯ | ◯ |
| | 2. Texture | ◯ | ◯ | ◯ | ◯ |
| | 3. Cold feel | ◯ | ◯ | ◯ | ◯ |
| | 4. Stickiness | ◯ | ◯ | x | x |
| | 5. Easy removal | ◯ | ◯ | Δ | Δ |

As shown in Table 7, Example 29 and Example 30 containing N-palmitoyl-Gly-His showed good results in each of easy application, texture, cold feel, stickiness, and easy removal.

In contrast, Comparative Example 9 and Comparative Example 10 without palmitoyl-Gly-His had good results in easy application, texture, and cold feel, but the gel itself had stickiness and had problems in a feel in use. Applying the gel sheet onto skin caused the gel to be twisted, and the gel sheet also had problems in removal.

After the sensory test, each sheet of Examples and Comparative Examples caused no skin trouble such as skin irritation and itchiness.

Example 31

Wound Dressing Base Material Evaluation of N-Palmitoyl-Gly-His Gel Sheet

<Preparation of N-Palmitoyl-Gly-His Gel Frozen-Thawed Gel Sheet>

Into a screw tube (manufactured by Maruemu Corporation, No. 5), 0.1 g of N-palmitoyl-Gly-His synthesized above, 1 g of PVA (manufactured by Wako Pure Chemical Industries, Ltd., average degree of polymerization n=1,500 to 1,800), and 8.9 g of 50 mM phosphate buffer solution (manufactured by Wako Pure Chemical Industries, Ltd., pH 7.4) were charged. The mixture was heated (at 90° C. for 60 minutes) in a dry bath incubator (manufactured by First Gene) to be dissolved. Into a petri dish (diameter 85 mm×height 15 mm), 10 mL of the solution was transferred and was allowed to stand and cool. After 15 hours, the gelation was ascertained by inversion method. At the time, a sample without flowability was considered to be a gel. Next, the gel was frozen at −20° C. for 15 hours, and then was thawed for 1 hour at room temperature, thereby affording a translucent gel sheet.

<Preparation of PVA Gel Frozen-Thawed Gel>

Into a screw tube (manufactured by Maruemu Corporation, No. 5), 1 g of PVA (manufactured by Wako Pure Chemical Industries, Ltd., average degree of polymerization n=1,500 to 1,800) and 8.8 g of 50 mM phosphate buffer solution (manufactured by Wako Pure Chemical Industries, Ltd., pH 7.4) were charged. The mixture was heated (at 90° C. for 60 minutes) in a dry bath incubator (manufactured by First Gene) to be dissolved. Into a petri dish (diameter 85 mm×height 15 mm), 10 mL of the solution was transferred and was allowed to stand and cool. After 15 hours, the gelation was ascertained by inversion method. At the time, a sample without flowability was considered to be a gel, Next, the gel was frozen at −20° C. for 15 hours, and then was thawed for 1 hour at room temperature, thereby affording a transparent gel.

<Preparation Method of Wound Model>

Under anesthesia with Nembutal (manufactured by Dainippon Sumitomo Pharma Co., Ltd, 1.3 μL/g intramuscular administration), hair on the back of a ddy strain male mouse (Kyudo Co., Ltd., 5-week old, n=8) was removed, and the epidermis of the back of the mouse was exfoliated with a pair of medical scissors disinfected with ethanol, thereby preparing a disk-like wound having a diameter of about 10 mm. Next, over the whole wound face, an N-palmitoyl-Gly-His gel frozen-thawed sheet, a hydrocolloid material (Kizu Power Pad, manufactured by Johnson & Johnson K.K.), a PVA cross-linked hydrogel (Viewgel, manufactured by Nichiban Co., Ltd), or a PVA gel frozen-thawed gel was applied as a dressing, and a fabric adhesive tape (manufactured by Nichiban Co., Ltd.) was applied onto the dressing so that each dressing was not removed.

<Healing Effect of Each Dressing on Wound Model and Number of Days for 50% Wound Healing>

Figure 13:
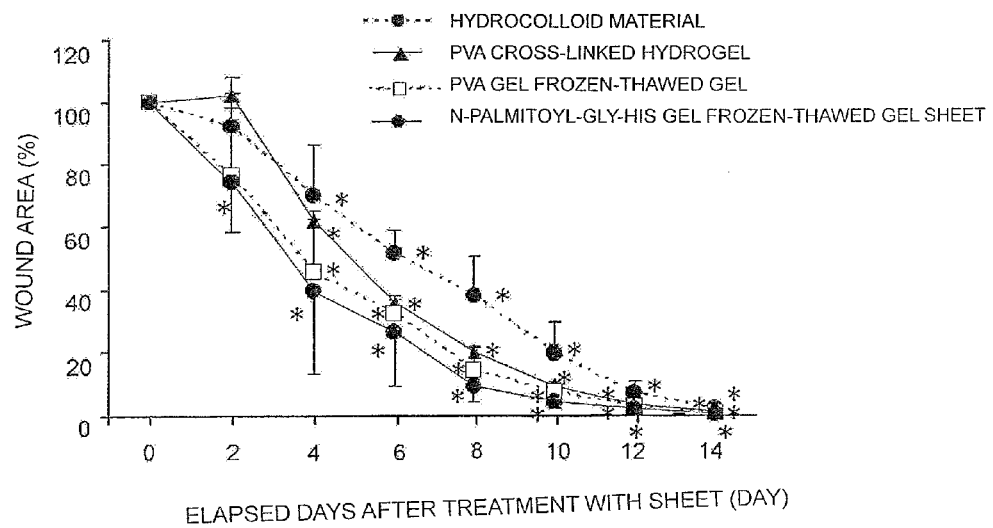
FIG. 13 is a graph showing healing effects of four dressings and showing a wound area (%) with respect to elapsed days (horizontal axis) after the treatment with sheets.
Figure 14:
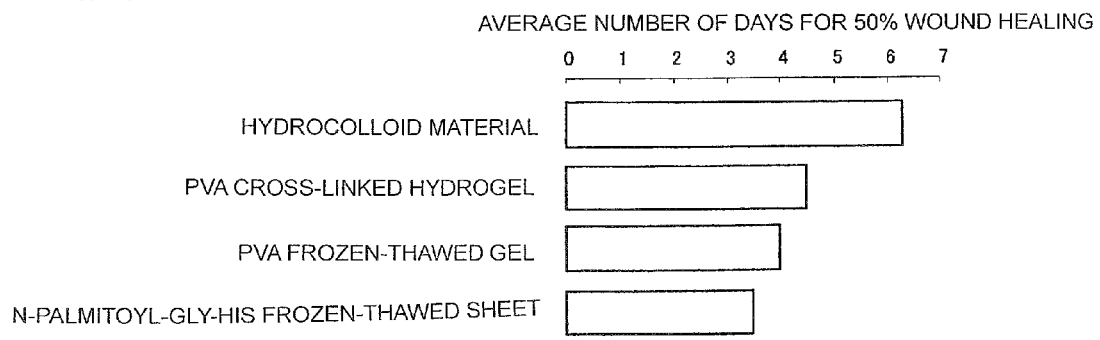
FIG. 14 is a graph showing the healing effects of four dressings and showing each average number of days for 50% wound healing.

Each dressing was exchanged every 2 days and the healing effect was analyzed. For the analysis, the wound area analysis by image processing software Image J, the analysis of the number of days for 50% wound healing, and the evaluation of a pathological tissue were carried out, and the wound healing effect of each dressing was observed. For the statistic calculation in the wound area analysis, t-test (statistical test tool for averages in a pair of samples) was carried out using Microsoft Office Excel 2003, and $P<0.05$ was regarded as a statistically significant difference. FIG. 13 and FIG. 14 show the obtained results. In FIG. 13, a result having a statistically significant difference is shown with *.

As shown in FIG. 13, the N-palmitoyl-Gly-His gel frozen-thawed gel sheet showed significant healing effect from day 2 after treatment in the wound area analysis, and the PVA gel frozen-thawed gel showed the tendency of the healing effect next to the N-palmitoyl-Gly-His gel frozen-thawed gel sheet. In contrast, the hydrocolloid material and the PVA cross-linked hydrogel showed significant effect from day 4.

As shown in FIG. 14, the N-palmitoyl-Gly-His gel frozen-thawed sheet had an average number of days for 50% wound healing smaller than those of the PVA gel frozen-thawed gel, the hydrocolloid material, and the PVA cross-linked hydrogel.

From these results, it is believed that the N-palmitoyl-Gly-His gel frozen-thawed sheet is useful as a wound dressing base material and using the sheet is expected to achieve earlier healing of a wound.

Example 32

Wound Skin Regeneration Effect of N-Palmitoyl-Gly-His Frozen-Thawed Gel Sheet Using a freezing microtome (manufactured by Leica, CM1510), each frozen section (8 μm) was prepared from a normal mouse skin and respective mouse skins after 4 days of the dressing treatment in four groups of mice used for the wound model in Example 31 (the N-palmitoyl-Gly-His gel frozen-thawed sheet dressing, the hydrocolloid material dressing, the PVA cross-linked hydrogel dressing, and the PVA gel frozen-thawed gel dressing). Each frozen section was stained with a Mayer's hematoxylin solution (manufactured by Wako Pure Chemical Industries, Ltd.) for 4 minutes, and then washed with water. The washed section was stained with 1% eosin Y solution (manufactured by Wako Pure Chemical Industries, Ltd.) for 1 minute, and then washed with water. The section was dehydrated with 95% ethanol and 99% ethanol. The section was stained with hematoxylin-eosin (HE staining), and was observed under an inverted microscope (manufactured by Olympus Corporation, IX70). The obtained results are shown in FIG. 15 (normal mouse skin) and FIG. 16 (wound model skins after 4 days of dressing treatment).

Figure 15:
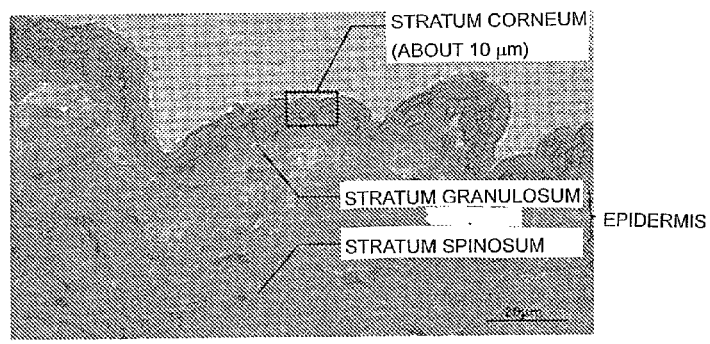
FIG. 15 is a photograph of an HE-stained normal skin of a normal mouse observed under a microscope.

As shown in FIG. 15, the microscope observation image of the HE-stained normal skin of a normal mouse shows the stratum corneum and the stratum granulosum and stratum spinosum of the epidermis.

Figure 16:
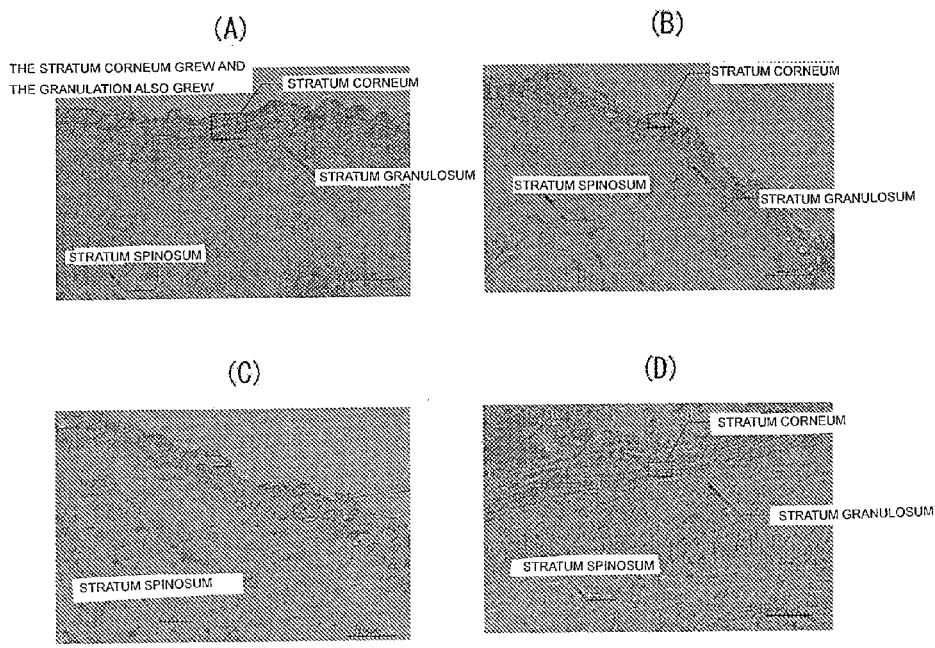
FIG. 16 shows photographs of HE-stained mouse wound skins after 4 days of wound and dressing treatment of wound model mice observed under a microscope (dressing base material.

Here, from the observation of the pathological tissue images (microscope observation images of HE stained tissues) of the mouse wound skins after 4 days of the wound and dressing treatment shown in FIG. 16, in the skin (FIG. 16A) dressed with the N-palmitoyl-Gly-His frozen gel and thawed gel sheet, the growth of the stratum corneum and the growth of the granulation are observed, and the obtained image is similar to a normal skin image. In contrast, the image from the PVA gel frozen-thawed gel (B) shows that cells move from the stratum granulosum to the upper layer and keratinization starts, the image from the hydrocolloid material (C) shows that no stratum corneum is formed, and the image from the PVA cross-linked hydrogel (D) shows that cells move from the stratum granulosum to the upper layer and keratinization starts.

In these observations, it is ascertained that the N-palmitoyl-Gly-His frozen gel and thawed sheet achieves rapid skin regeneration in a wound area.

Example 33

Blood Cell Trap Effect of N-Palmitoyl-Gly-His Gel

<Preparation of Mixed Sample of N-Palmitoyl-Gly-His Gel and Guinea Pig Stored Blood>

Into a screw tube (manufactured by Maruemu Corporation, No. 5), 0.3 g N-palmitoyl-Gly-His synthesized above and 9.7 g of 50 mM phosphate buffer solution (manufactured by Wako Pure Chemical Industries, Ltd., pH=7.4) were charged. The mixture was heated (at 90° C. for 60 minutes) in an aluminum block bath (manufactured by Taitec Co., Ltd.) to be dissolved, and then was allowed to stand and cool at room temperature. After 15 hours, the gelation was ascertained by inversion method. At the time, a sample without flowability was considered to be a gel. Next, at the center of the gel prepared in the screw tube, a hole having a diameter of 7 mm and a depth 5 mm was formed. Into the hole, 150 of guinea pig stored blood was dropped, and the whole was left at room temperature overnight, followed by the evaluation of blood coagulation described later.

The guinea pig stored blood (manufactured by Nippon Biotest Laboratories Inc.) was prepared by aseptic blood collection and immediate addition of an anticoagulant preservative solution (5.5 g of citric acid, 80 g of sodium citrate, 42 g of sodium chloride, 205 g of glucose, and 10 L of purified water) in a ratio of the blood and the solution of 1:1.

<Preparation of Mixed Sample of 10% Carboxymethyl Cellulose (Hereinafter Called CMC) and Guinea Pig Stored Blood>

Into a screw tube (manufactured by Maruemu Corporation, No. 5), 1 g of CMC (manufactured by Wako Pure Chemical Industries, Ltd.) and 9 g of 50 mM phosphate buffer solution (manufactured by Wako Pure Chemical Industries, Ltd., pH=7.4) were charged. The mixture was heated (at 90° C. for 120 minutes) in an aluminum block bath (manufactured by Taitec Co., Ltd.) to be dispersed. The dispersed liquid was allowed to stand and cool at room temperature. After 15 hours, the gelation was ascertained by inversion method. At the time, a sample without flowability was considered to be a gel.

Next, at the center of the gel prepared in the screw tube, a hole having a diameter of 7 mm and a depth 5 mm was formed. Into the hole, 150 μl of guinea pig stored blood was dropped, and the whole was left at room temperature overnight, followed by the evaluation of blood coagulation described later.

Figure 17:
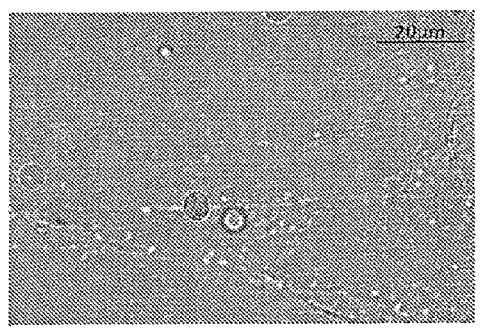
FIG. 17 shows photographs showing the red blood cell trap effect of a mixed sample of an N-palmitoyl-Gly-His gel and guinea pig stored blood (FIG. 17A) and a mixed sample of 10% CMC and guinea pig stored blood (FIG. 17B) observed under an optical microscope.
Figure 17:
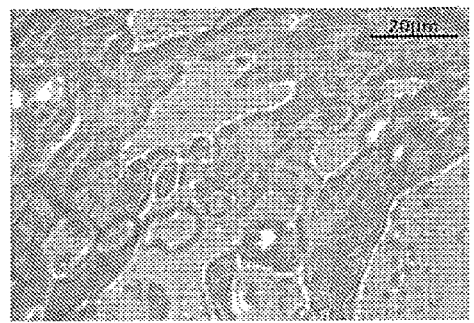

Each of the mixed sample of N-palmitoyl-Gly-His gel and guinea pig stored blood and the mixed sample of 10% CMC and guinea pig stored blood prepared by the method above was applied onto a slide glass and was evenly spread with a cover glass. Then, each sample was subjected to bright field observation under an optical microscope (manufactured by Leica, DM2500 (×1,000)). FIG. 17 show the obtained results.

Figure 18:
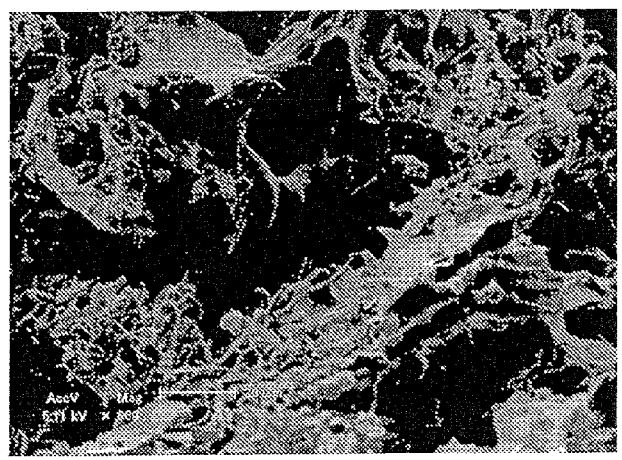
FIG. 18 is a photograph of a mixed sample of an N-palmitoyl-Gly-His and guinea pig stored blood observed under a scanning electron microscope with an energy dispersive X-ray analyzer.

Next, the mixed sample of N-palmitoyl-Gly-His gel and guinea pig stored blood was immersed in liquid nitrogen for 20 minutes, then was freeze dried with a freeze dryer (manufactured by EYELA, FDU-1100) for 16 hours, and was applied onto a cover glass. The cover glass was attached to a sample plate and was subjected to low vacuum observation (×600) under a scanning electron microscope (SEM) with an energy dispersive X-ray analyzer (manufactured by Shimadzu Corporation). FIG. 18 shows the obtained result.

As shown in FIG. 17, the optical microscope observation shows that the fibrous structure constituting the N-palmitoyl-Gly-His gel traps red blood cells (FIG. 17A), whereas CMC shows hemolysis that breaks red blood cells (FIG. 17B).

As shown in FIG. 18, the SEM observation shows the adhesion of blood cell components to the fibrous structure constituting the N-palmitoyl-Gly-His gel.

These results suggest the followings. The fibrous structure constituting the N-palmitoyl-Gly-His gel physically traps blood cell components. This controls the immune environment in a wound area. In other words, the N-palmitoyl-Gly-His gel has an effect of accelerating skin regeneration, for example, the effect of controlling excess inflammatory reaction due to immune reaction and the effect of controlling inflammatory cell functions.

As described above, the gel sheet of the present invention provides the physical control mechanism to affect blood cells, thus providing the efficacy as a wound dressing base material. Hence, the gel sheet is believed to be useful as a novel wound healing acceleration base material that can maintain a moist environment without adhesion to a wound surface and can rapidly heal a wound with a little pain, and also as a skin protection material and a skin care material that are used after surgery or in order to prevent skin problems.

The invention claimed is:

1. A gel sheet comprising:
a lipid peptide gelator including a low molecular weight lipid peptide having a molecular weight of 1,000 or less or a pharmaceutically usable salt of the lipid peptide; and
a polymeric compound, wherein:
the polymeric compound is included in an amount of more than 1% (w/w) and less than 50% (w/w) with respect to a total mass of the gel sheet; and
the low molecular weight lipid peptide is a lipid peptide of Formula (1) or a pharmaceutically usable salt of the lipid peptide:

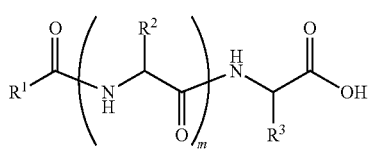

where:
$R^1$ is a $C_{9-23}$ aliphatic group;
each of $R^2$ and $R^3$ is independently a hydrogen atom, a methyl group, an ethyl group, a $C_{3-7}$ alkyl group optionally having a $C_{1-3}$ branched chain, a phenylmethyl group, a phenylethyl group, or a —$(CH_2)n$-X group;
at least one of $R^2$ and $R^3$ being a —$(CH_2)n$-X group;
n is a number of 1 to 4;
X is an amino group, a guanidino group, a carbamoyl group, a 5-membered cyclic group or 6-membered cyclic group optionally having one to three nitrogen atoms, or a condensed heterocyclic group composed of a 5-membered ring and a 6-membered ring; and
m is 1.

2. The gel sheet according to claim 1, wherein the polymeric compound is included in an amount of 2% (w/w) to 20% (w/w) with respect to the total mass of the gel sheet.

3. The gel sheet according to claim 1, wherein the polymeric compound is selected from a linear polymeric compound having a hydroxy group and polysaccharides.

4. The gel sheet according to claim 3, wherein the polymeric compound is polyvinyl alcohol, gum arabic, or gelatin.

5. The gel sheet according to claim 1, wherein $R^2$ is a hydrogen atom, a methyl group, an i-propyl group, an i-butyl group, or a sec-butyl group.

6. The gel sheet according to claim 1, wherein $R^3$ is a 4-aminobutyl group, 4-imidazolemethyl group, a carbamoylmethyl group, a 2-carbamoylethyl group, or a 3-indolemethyl group.

7. The gel sheet according to claim 1, wherein $R^1$ is a $C_{13-17}$ aliphatic group, $R^2$ is a hydrogen atom, a methyl group, or an i-propyl group, and $R^3$ is a 4-aminobutyl group, a 4-imidazolemethyl group, or a 3-methylindole group.

8. The gel sheet according to claim 1, wherein $R^2$ is a hydrogen atom and $R^3$ is a 4-imidazolemethyl group.

9. The gel sheet according to claim 1, further comprising water, an alcohol, a polyhydric alcohol, a hydrophilic organic solvent, a hydrophobic organic solvent, or a mixed solution of two or more of these.

10. The gel sheet according to claim 9, comprising water or a mixed solution of water and at least one selected from the group consisting of an alcohol, a polyhydric alcohol, an oil and fat, a silicone oil, and an ester solvent.

11. The gel sheet according to claim 10, comprising water or a mixed solution of water and at least one selected from the group consisting of ethanol, 2-propanol, oleyl alcohol, phenoxy alcohol, glycerin, propylene glycol, polyethylene glycol, 1,3-butanediol, aqua jojoba oil, castor oil, olive oil, a silicone oil, and propylene glycol alginate.

12. The gel sheet according to claim 9, comprising a polyhydric alcohol or a mixed solution of a polyhydric alcohol and at least one selected from the group consisting of an alcohol, an oil and fat, a silicone oil, and an ester solvent.

13. The gel sheet according to claim 12, comprising at least one polyhydric alcohol selected from the group consisting of glycerin, propylene glycol, polyethylene glycol, and 1,3-butanediol or a mixed solution of at least one of the polyhydric alcohols and at least one selected from the group consisting of ethanol, 2-propanol, oleyl alcohol, phenoxy alcohol, aqua jojoba oil, castor oil, olive oil, a silicone oil, and propylene glycol alginate.

14. The gel sheet according to claim 9, comprising a solution containing water and one lactic acid salt selected from the group consisting of potassium lactate, sodium lactate, and calcium lactate.

15. The gel sheet according to claim 14, further comprising at least one polyhydric alcohol selected from the group consisting of glycerin, propylene glycol, polyethylene glycol, and 1,3-butylene glycol.

16. A laminate comprising:
the gel sheet according to claim 1; and
a support medium laminated on the sheet, the support medium including a nonwoven fabric, a film, or a foam.

17. The laminate according to claim 16, further comprising a release film laminated on a surface on the opposite side of the gel sheet from the support medium.

18. The laminate according to claim 16, wherein the support medium is selected from polyurethane, PVA, polypropylene, cellulose, and a laminated support medium of these.

19. The gel sheet according to claim 1, wherein the gel sheet is a wound dressing sheet.

20. The gel sheet according to claim 1, wherein the gel sheet is a skin protection sheet or a skin care sheet.

21. The laminate according to claim 16, wherein the laminate is used for a wound dressing.

22. The laminate according to claim 16, wherein the laminate is used for a skin protection sheet or a skin care sheet.

* * * * *